United States Patent
Harrysson et al.

(10) Patent No.: US 8,206,967 B2
(45) Date of Patent: Jun. 26, 2012

(54) METHOD FOR PRODUCTION OF RECOMBINANT HUMAN THROMBIN

(75) Inventors: Anna Harrysson, Mölndal (SE); Ann Lövgren, Mölndal (SE)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 12/167,614

(22) Filed: Jul. 3, 2008

(65) Prior Publication Data

US 2009/0047273 A1    Feb. 19, 2009

Related U.S. Application Data

(60) Provisional application No. 60/948,207, filed on Jul. 6, 2007.

(51) Int. Cl.
| | |
|---|---|
| C12N 9/74 | (2006.01) |
| C12N 9/48 | (2006.01) |
| C12N 9/02 | (2006.01) |
| C12N 15/00 | (2006.01) |
| C12N 5/02 | (2006.01) |
| C12P 21/06 | (2006.01) |
| C12P 21/04 | (2006.01) |
| C07H 21/04 | (2006.01) |
| C07K 1/00 | (2006.01) |
| A61K 38/48 | (2006.01) |
| A61K 38/43 | (2006.01) |

(52) U.S. Cl. ....... 435/214; 435/212; 435/189; 435/69.1; 435/69.6; 435/320.1; 435/325; 536/23.1; 536/23.2; 530/350; 424/94.64; 424/94.1

(58) Field of Classification Search ................ 435/214, 435/212, 189, 69.1, 69.6, 320.1, 325; 536/23.1, 536/23.2; 530/350; 424/94.64, 94.1
See application file for complete search history.

(56) References Cited

U.S. PATENT DOCUMENTS

| | | | |
|---|---|---|---|
| 4,404,187 | A | 9/1983 | Schwinn et al. |
| 4,599,308 | A | 7/1986 | Hamer et al. |
| 4,784,950 | A | 11/1988 | Hagen et al. |
| 5,118,614 | A | 6/1992 | Rybák et al. |
| 5,122,458 | A | 6/1992 | Post et al. |
| 5,648,254 | A | 7/1997 | Mulvihill et al. |
| 5,866,122 | A | 2/1999 | Turecek et al. |
| 5,958,893 | A | 9/1999 | Welsh et al. |
| 5,965,789 | A | 10/1999 | Lubon et al. |
| 6,039,945 | A | 3/2000 | Turecek et al. |
| 6,165,974 | A | 12/2000 | Turecek et al. |
| 6,224,862 | B1 | 5/2001 | Turecek et al. |
| 6,224,864 | B1 | 5/2001 | Argoudelis et al. |
| 6,342,372 | B1 | 1/2002 | Dubensky, Jr. et al. |
| 6,413,737 | B1 * | 7/2002 | Olsen et al. ................. 435/68.1 |
| 7,482,141 | B2 | 1/2009 | Stafford et al. |
| 7,842,477 | B2 | 11/2010 | Fenge et al. |
| 7,989,193 | B2 | 8/2011 | Lövgren |
| 2002/0106381 | A1 | 8/2002 | High |
| 2004/0197858 | A1 * | 10/2004 | Yonemura et al. ........... 435/69.1 |
| 2005/0164367 | A1 * | 7/2005 | Fenge et al. ................... 435/232 |
| 2008/0045453 | A1 | 2/2008 | Drohan et al. |
| 2008/0312127 | A1 | 12/2008 | Lovgren |
| 2009/0047273 | A1 | 2/2009 | Harrysson et al. |
| 2011/0092429 | A1 | 4/2011 | Fenge et al. |

FOREIGN PATENT DOCUMENTS

| | | |
|---|---|---|
| EP | 0052827 | 6/1982 |
| EP | 0607392 | 7/1994 |
| EP | 0700682 | 3/1996 |
| EP | 1407780 | 4/2004 |
| EP | 1405910 | 7/2004 |
| EP | 1405912 | 7/2004 |
| EP | 1676911 | 5/2006 |
| WO | WO88/03926 | 6/1988 |
| WO | WO89/12685 | 12/1989 |
| WO | WO92/01795 | 2/1992 |
| WO | WO92/19636 | 11/1992 |
| WO | WO96/34966 | 11/1996 |
| WO | WO99/33983 | 7/1999 |
| WO | WO 01/04146 | 1/2001 |
| WO | WO01/07068 | 2/2001 |
| WO | WO02/29045 | 4/2002 |
| WO | WO02/29083 | 4/2002 |
| WO | WO2005/030039 | 4/2005 |
| WO | WO2005/038019 | 4/2005 |
| WO | WO2005/040367 | 5/2005 |
| WO | WO2006/067116 | 6/2006 |
| WO | WO2006/110083 | 10/2006 |
| WO | WO2007/065173 | 6/2007 |

OTHER PUBLICATIONS

Broun et al., Catalytic plasticity of fatty acid modification enzymes underlying chemical diversity of plant lipids. Science, 1998, vol. 282: 1315-1317.*
Seffernick et al., Melamine deaminase and Atrazine chlorohydrolase: 98 percent identical but functionally different. J. Bacteriol.,2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Gustafsson et al., Codon bias and heterologous protein expression. TRENDS in Biotechnol., 2004, vol. 22(7): 346-353.*
Koresawa et al., Synthesis of a new cre recombinase gene based on optimal codon usage for mammalian systems. J. Biochem., 2000, vol. 127: 367-372.*
McCawley et al., Matrix metalloproteinases: they're not just for matrix anymore!. Curr. Opinion Cell Biol., 2001, vol. 13: 534-540.*
Newby AC., Matrix matalloproteinases regulate migration, proliferation, and death . . . Cardiovascular Res., 2006, vol. 69: 614-624.*
Nishida et al., "cDNA cloning and deduced amino acid sequence of prothrombin activator (ecarin) from Kenyan *Echis carinatus* venom," Biochem., 34:1771-1778 (1995).
Pei et al., "Expression, isolation, and characterization of an active site (serine 528-alanine) mutant of recombinant bovine prothrombin," J. Biol. Chem., 266:9598-9604 (1991).

(Continued)

*Primary Examiner* — Ganapathirama Raghu
(74) *Attorney, Agent, or Firm* — Fish & Richardson P.C.

(57) ABSTRACT

The present invention relates to compositions and methods for producing recombinant human thrombin using recombinant ecarin.

36 Claims, 10 Drawing Sheets

OTHER PUBLICATIONS

Yonemura et al., "Preparation of recombinant alpha-thrombin:high-level expression of recombinant human prethrombin-2 and its activation by recombinant ecarin," J. Biochem., 135:577-582 (2004).

Bajaj et al. "Isolation and Characterization of Human Factor VII. Activation of Factor VII by Factor X" J. Biotechnol. 1981 (256) 253-259.

Bajaj et al. "A Simplified Procedure for Purification of Human Prothrombin, Factor IX and Factor X" Prep. Biochem. 1981 (11) 397-412.

Bandyopadhyay et al. "γ-Glutamyl carboxylation: an extracellular posttranslational modification that antedates the divergence of molluscs, anthropods, and chordates" Proc. Natl. Acad. Sci. 2002 (99) 1264-1269.

Begley et al. "A conserved motif within the vitamin K-dependent carboxylase gene is widely distributed across animal phyla" J. Biol. Chem. 2000 (275) 36245-36249.

Bentley et al. "Differential Efficiency of Expression of Humanized Antibodies in Transient Transfected Mammalian Cells" Hybridoma. 1998 (17) 559-567.

Bishop et al. "Comparison of Recombinant Human Thrombin and Plasma-Derived Human α-Thrombin" Sem Throm Hem. 2006 (32) 86-97.

Camire et al. "Enhanced γ-Carboxylation of Recombinant Factor X Using a Chimeric Construct Containing the Prothrombin Propeptide" Biochemistry. 2000 (39) 14322-14329.

Clark et al. "The Secreted Protein Discovery Initiative (SPDI), a Large-Scale Effort to Identify Novel Human Secreted and Transmembrane Proteins: A Bioinformatics Assessment" Genome Res. 2003 (13) 2265-2270.

Cote et al. "Characterization of a stable form of human meizothrombin derived from recombinant prothrombin (R155A, R271A, and R284A)," J. Biol. Chem. 1994 (269) 11374-11380.

Czerwiec et al. "Expression and characterization of recombinant vitamin K-dependent γ-glutamyl carboxylase from an invertebrate, *Conus textile*" Eur. J. Biochem. 2002 (269) 6162-6172.

Fair et al. "Biosynthesis and Secretion of Factor VII, Protein C, Protein S, and the Protein C Inhibitor From a Human Hepatoma Cell Line" Blood. 1986 (67) 64-70.

Falkner et al. "High Level Expression of Active Human Prothrombin in a Vaccine Virus Expression System" Thrombosis and Haemostasis. 1992 (68) 119-124.

Fischer et al. "Purification of recombinant human coagulation factors II and IX and protein S expressed in recombinant Vaccinia virus-infected Vero cells" Journal of Biotechnology. 1995 (38) 129-136.

Gamma Glutamyl Carboxylase. UniPro Database. [online], [retrieved on Jan. 14, 2010] Retrieved from the UniPro Database using Internet <URL: http://www.uniprot.org/uniprot/?query=gamma+glutamyl+carboxylase&sort=score>.

Hallgren et al. "Carboxylase overexpression effects full carboxylation but poor release and secretion of a factor IX: implications for the release of vitamin K-dependent proteins" Biochemistry. 2002 (41) 15045-15055.

Harvey et al. "Mutagenesis of the γ-carboxyglutamic acid domain of human factor VII to generate maximum enhancement of the membrane contact site" J. Biol. Chem. 2003 (278) 8363-8369.

Hellstern et al. Preface Thrombosis Research. 1999 (95) S1.

Hellstern et al. "Prothrombin Complex Concentrates: Indications, Contraindications, and Risks: A Task Force Summary" Thrombosis Research. 1999 (95) S3-S6.

Hellstern "Production and Composition of Prothrombin Complex Concentrates: Correlation between Composition and Therapeutic Efficiency" Thrombosis Research. 1999 (95) S7-S12.

Herlitschka et al. "Overexpression of human prothrombin in permanent cell lines using a dominant selection/amplification fusion marker" Protein Expression and Purification. 1996 (8) 358-364.

Himmelspach et al. "A Fully Recombinant Partial Prothrombin Complex Effectively Bypasses fVII In Vitro and In Vivo" Thromb Haemost. 2002 (88) 1003-1011.

Jorgensen et al. "Expression of completely γ-carboxylated recombinant human prothrombin" J. Biol. Chem. 1987 (262):6729-6734.

Kaufman et al. "Expression, Purification, and Characterization of Recombinant γ-Carboxylated Factor IX Synthesized in Chinese Hamster Ovary Cells" J. Biol. Chem. 1986 (261) 9622-9628.

Kini et al. "The intriguing world of prothrombin activators from snake venom" Toxicon. 2005 (45) 1133-1145.

Köhler "Thrombogenicity of Prothrombin Complex Concentrates" Thrombosis Research. 1999 (95) S13-S17.

Kozak "Point Mutations Define a Sequence Flanking the AUG Initiator Codon That Modulates Translation by Eukaryotic Ribosomes" Cell. 1986 (44) 283-292.

Kozak "Downstream Secondary Structure Facilitates Recognition of Intiator Codons by Eukaryotic Ribosomes" Proceedings of the National Academy of Sciences of the United States of America. 1990 (87) 8301-8305.

Kozak "An analysis of 5'-noncoding sequences from 699 vertebrate messenger RNAs" Nucleic Acids Research. 1987 (15) 8125-8148.

Li et al. "Identification of the gene for vitamin K epoxide reductase" Nature. 2004 (427) 541-544.

Lingenfelter et al. "Isolation of the Human γ-Carboxylase and a γ-Carboxylase-Associated Protein from Factor IX-Expressing Mammalian Cells" Biochemistry. 1996 (35) 8234-8243.

Lucas et al. "High-level production of recombinant proteins in CHO cells using a dicistronic DHFR intron expression vector" Nucleic Acids Research. 1996 (24) 1774-1779.

Malhotra et al. "The kinetics of activation of normal and γ-carboxyglutamic acid-deficient prothrombins," J. Biol. Chem. 1985 (260) 279-287.

Melcher et al. "Plasmid vectors with a 5'-hybrid intron facilitate high-level glycoprotein expression in CHO-cells" Biochimica et Biophysica Acta. 2002 (1575) 49-53.

Munns et al. "Vitamin K-dependent synthesis and modification of precursor prothrombin in cultured H-35 hepatoma cells" Proc. Natl. Acad. Sci. 1976 (73) 2803-2807.

Pejler et al. "Thrombin Is Inactivated by Mast Cell Secretory Granule Chymase" J. Biol. Chem. 1993 (268) 11817-11822.

Rehemtulla et al. "In vitro and in vivo functional characterization of bovine vitamin K-dependent γ-carboxylase expressed in Chinese hamster ovary cells" Proc. Natl. Acad. Sci. 1993 (90) 4611-4615.

Robertson "Genes Encoding Vitamin-K Epoxide Reductase Are Present in Drosophila and Trypanosomatid Protists" Genetics. 2004 (168) 1077-1080.

Roddie at al. "Haemostasis and thrombosis: Recombinant coagulation factors" Blood Reviews. 1997 (11) 169-177.

Rost et al. "Mutations in *VKORC1* cause warfarin resistance and multiple coagulation factor deficiency type 2" Nature. 2004 (427) 537-541.

Rouet et al. "A Potent Enhancer Made of Clustered Liver-specified Elements in the Transcription Control Sequences of Human α1-Microglobulin/Bikunin Gene" The Journal of Biological Chemistry. 1992 (267) 20765-20773.

Russo et al. "Biologically active recombinant prothrombin and antithrombin III expressed in a human hepatoma/vaccinia virus system" Biotechnology and Applied Biochemistry. 1991 (14) 222-223.

Russo et al. "Stable expression and purification of a secreted human recombinant prethrombin-2 and its activation to thrombin" Protein Expression and Purification. 1997 (10) 214-225.

Sadler "K is for koagulation" Nature. 2004 (427) 493-494.

Scharrer "The Need for Highly Purified Products to Treat Hemophilia B" Acta Haematol. 1995 (94) 2-7.

Scharrer et al. "Products used to treat hemophilia: evolution of treatment for hemophilia A and B" in: Lee et al. eds., Textbook of Hemophilia (New York, Blackwell, 2005), Ch. 23, pp. 131-135.

Slimko et al. "Codon optimization of Caenorhabditis elegans GluCl ion channel genes for mammalian cells dramatically improves expression levels" J. Neuroscience Methods. 2003 (124) 75-81.

Stanley et al. "The propeptides of the vitamin K-dependent proteins possess different affinities for the vitamin K-dependent carboxylase" J. Biol. Chem. 1999 (274) 16940-16944.

Strausberg et al. "Generation and initial analysis of more than 15,000 full-length human and mouse cDNA sequences" PNAS. 2002 (99) 16899-16903.

Sun et al. "Vitamin K epoxide reductase significantly improves carboxylation in a cell line overexpressing factor X" Blood. 2005 (106) 3811-3815.

Tans et al. "Prothrombin Activation by Snake Venom Proteases" J. Toxicol.-Toxin Reviews. 1993 (12) 155-173.

Umaña et al. "Tetracycline-Regulated Overexpression of Glycosyltransferases in Chinese Hamster Ovary Cells" Biotechnology and Bioengineering. 1999 (65) 542-549.

Vo et al. "Undercarboxylation of recombinant prothrombin revealed by analysis of γ-carboxyglutamic acid using capillary electrophoresis and laser-induced fluorescence" Febs Letters. 1999 (445) 256-260.

Wajih et al. "Engineering of a Recombinant Vitamin K-dependent γ-Carboxylation System with Enhanced γ-Carboxyglutamic Acid Forming Capacity" J. Biol. Chem. 2005 (280) 10540-10547.

Wajih et al. "Increased Production of Functional Recombinant Human Clotting Factor IX by Baby Hamster Kidney Cells Engineered to Overexpress VKORC1, the Vitamin K 2,3-Expoxide-reducing Enzyme of the Vitamin K Cycle" J. Biol. Chem. 2005 (280) 31603-31607.

Wajih et al. "The Inhibitory Effect of Calumenin on the Vitamin K-dependent γ-Carboxylation System" J. Biol. Chem. 2004 (279) 25276-25283.

Walker at al., "On a potential global role for vitamin K-dependent γ-carboxylation in animal systems" J. Biol. Chem. 2001 (276) 7769-7774.

Wallin et al. "Vitamin K-dependent Carboxylation and Vitamin K Metabolism in Liver" J. Clin. Invest. 1985 (76) 1879-1884.

Wallin et al. "Vitamin K 2,3-epoxide reductase and the vitamin K-dependent γ-carboxylation system" Thrombosis Research. 2003 (108) 221-226.

Wang et al. "The Growth Inhibitory Effects of Vitamins K and Their Actions on Gene Expression" Hepatology. 1995 (22) 876-882.

Wu et al. "Cloning and expression of the cDNA for human γ-glutamyl carboxylase" Science. 1991 (254) 1634-1636.

Wu et al. "N-Glycosylation contributes to the intracellular stability of prothrombin precursors in the endoplasmic reticulum" Thrombosis Research. 1999 (96) 91-98.

Zhang et al. "Relative Promoter Strengths in Four Human Prostate Cancer Cell Lines Evaluated by Particle Bombardment-Mediated Gene Transfer" The Prostate. 2002 (51) 286-292.

PCT Written Opinion for Application No. PCT/SE2008/050836, dated Jan. 21, 2010, 10 pages.

Nucleotide sequence of human prothrombin (EBI accession No. AJ972449), last modified Oct. 21, 2008, 8 pages.

Amino acid sequence for wild type ecarin (EBI accession No. Q90495), last modified Jan. 19, 2010, 5 pages.

USPTO Restriction Requirement in U.S. Appl. No. 10/964,888, mailed Aug. 9, 2006, 10 pages.

Fish & Richardson P.C., Amendment in Reply to Restriction Requirement dated Aug. 9, 2006 in U.S. Appl. No. 10/964,888, filed Feb. 6, 2007, 11 pages.

USPTO Non-Final Office Action in U.S. Appl. No. 10/964,888, mailed Apr. 19, 2007, 17 pages.

Fish & Richardson P.C., Amendment in Reply to Action dated Apr. 19, 2007 in U.S. Appl. No. 10/964,888, filed Oct. 18, 2007, 26 pages.

USPTO Non-Final Office Action in U.S. Appl. No. 10/964,888, mailed Jan. 28, 2008, 29 pages.

Fish & Richardson P.C., Amendment in Reply to Action dated Jan. 28, 2008 in U.S. Appl. No. 10/964,888, filed Apr. 28, 2008, 22 pages.

USPTO Final Office Action in U.S. Appl. No. 10/964,888, mailed Apr. 3, 2009, 6 pages.

Fish & Richardson P.C., Amendment in Reply to Action dated Apr. 3, 2009 in U.S. Appl. No. 10/964,888, filed Jun. 17, 2009, 15 pages.

USPTO Non-Final Office Action in U.S. Appl. No. 10/964,888, mailed Aug. 21, 2009, 5 pages.

Fish & Richardson P.C., Amendment in Reply to Action dated Aug. 21, 2009 in U.S. Appl. No. 10/964,888, filed Nov. 10, 2009, 17 pages.

USPTO Non-Final Office Action in U.S. Appl. No. 10/964,888, mailed Jan. 27, 2010, 9 pages.

USPTO Restriction Requirement in U.S. Appl. No. 11/572,870, mailed Apr. 2, 2009, 5 pages.

Fish & Richardson P.C., Response to Restriction Requirement and Preliminary Amendment dated Apr. 2, 2009 in U.S. Appl. No. 11/572,870, filed Sep. 25, 2009, 16 pages.

USPTO Non-Final Office Action in U.S. Appl. No. 11/572,870, mailed Jan. 26, 2010, 18 pages.

Fish & Richardson P.C., Amendment in Reply to Non-Final Action of Jan. 27, 2010 in U.S. Appl. No. 10/964,888, filed Apr. 14, 2010, 15 pages.

USPTO Notice of Allowance in U.S. Appl. No. 10/964,888, mailed Jul. 20, 2010, 6 pages.

Fish & Richardson P.C., Response to Notice of Allowance of Jul. 20, 2010 in U.S. Appl. No. 10/964,888, filed Oct. 20, 2010, 3 pages.

Fish & Richardson P.C., Amendment in Reply to Action of Jan. 26, 2010 in U.S. Appl. No. 11/572,870, filed May 26, 2010, 21 pages.

USPTO Final Office Action in U.S. Appl. No. 11/572,870, mailed Aug. 6, 2010, 18 pages.

USPTO Non-Final Office Action in U.S. Appl. No. 13/167,134, mailed Feb. 3, 2012, 16 pages.

Fish & Richardson P.C., RCE and Amendment in Reply to Action of Aug. 6, 2010 in U.S. Appl. No. 11/572,870, filed Feb. 7, 2011, 16 pages.

USPTO Notice of Allowance in U.S. Appl. No. 11/572,870, mailed Mar. 24, 2011, 8 pages.

* cited by examiner

WT
Score = 744 bits (387), Expect = 0.0
Identities = 1365/1848 (73%), Gaps = 0/1848 (0%)
Strand = Plus/Plus

```
AZ ecarin    1  ATGATCCAGATCCTGCTGGTGATCATCTGCCTGGCCGTGTTCCCCTACCAGGGCTGCTCC  60
                |||||||||| ||  |||| || || ||| | || || || || || || || |||||
WT ecarin    1  ATGATCCAGATTCTCTTGGTAATTATATGCTTAGCAGTTTTTCCATATCAAGGTTGCTCT  60

AZ ecarin   61  ATCATCCTGGGCAGCGGCAACGTGAACGACTACGAGGTGGTGTACCCCCAGAAGGTGACC  120
                || ||||||||    || || || || || || || || || ||||| || || || ||
WT ecarin   61  ATAATCCTGGGATCTGGGAATGTTAATGATTATGAAGTAGTGTATCCACAAAAAGTCACT  120

AZ ecarin  121  GCCCTGCCCAAGGGCGCCGTGCAGCAGCCCGAGCAGAAATACGAGGACGCCATGCAGTAC  180
                || ||||||||  || || ||  ||||||||| || ||  | || || ||||||| ||
WT ecarin  121  GCATTGCCCAAAGGAGCAGTTCAGCAGCCTGAGCAAAAGTATGAAGATGCCATGCAATAT  180

AZ ecarin  181  GAGTTCGAGGTGAAGGGCGAGCCCGTGGTGCTGCACCTGGAGAAGAACAAGGAGCTGTTC  240
                || || || |||||||| ||||| ||||| || || ||||| || || || || || ||
WT ecarin  181  GAATTTGAAGTGAAGGGAGAGCCAGTGGTCCTTCACCTAGAAAAAAATAAAGAACTTTTT  240

AZ ecarin    1  AGCGAGGACTACAGCGAGACCCACTACAGCAGCGACGACAGGGAGATCACCACCAACCCC  300
                  || || ||||| ||||| ||  ||     || || ||  || || || || |||||
WT ecarin    1  TCAGAAGATTACAGTGAGACTCATTATTCGTCTGATGACAGAGAAATTACAACAAACCCT  300

AZ ecarin    1  AGCGTGGAGGACCACTGCTACTACCACGGCCGGATCCAGAACGACGCCGAGAGCACCGCC  360
                   || |||| |||||||||| ||  || || ||||||||||||||  || || |  ||
WT ecarin    1  TCAGTTGAGGATCACTGCTATTATCATGGACGGATCCAGAATGATGCTGAGTCAACTGCA  360

AZ ecarin    1  AGCATCAGCGCCTGTAATGGCCTGAAGGGCCACTTCAAGCTGAGAGGCGAGACCTACTTC  420
                |||||||| ||  || |||| |||| ||||||||||||||||  |||| ||||| ||||
WT ecarin    1  AGCATCAGTGCATGCAATGGTTTGAAAGGACATTTCAAGCTTCGAGGGGAGACGTACTTT  420

AZ ecarin    1  ATCGAGCCCCTGAAGATCCCCGACAGCGAGGCCCACGCCGTGTACAAGTACGAGAACATC  480
                || || |||  ||||||| |||||| | ||||| ||||| || || |||| || |||||
WT ecarin    1  ATTGAACCCTTGAAGATTCCCGACAGTGAAGCCCATGCAGTCTACAAATATGAAAACATA  480

AZ ecarin    1  GAGAACGAGGACGAGGCCCCTAAGATGTGTGGCGTGACCCAGGACAACTGGGAGAGCGAC  540
                || || |||| || ||||| || |||||||||  ||  || ||||||||| |||||  |
WT ecarin    1  GAAAATGAGGATGAAGCCCCCAAAATGTGTGGGGTAACCCAGGATAATTGGGAATCAGAT  540

AZ ecarin    1  GAGCCCATCAAGAAAACCCTGGGCCTGATCGTGnnnnnnnnACGAGAGAAAGTTCGAGAAG  600
                || ||||||||  |||  ||||  ||||  | || || || || ||||  |||||||||
WT ecarin    1  GAACCCATCAAAAAGACTTTGGGGTTAATTGTTCCTCCTCATGAACGAAAATTTGAGAAA  600
```

FIG. 4A

```
AZ ecarin  1   AAGTTCATCGAACTGGTGGTCGTGGTGGACCACAGCATGGTGACCAAGTACAACAACGAC 660
               || ||||| || || || || || |||||||||||| ||||| || || |||||||| ||
WT ecarin  1   AAATTCATTGAGCTTGTCGTAGTTGTGGACCACAGTATGGTCACAAAATACAACAATGAT 660

AZ ecarin  1   AGCACCGCCATCAGGACCTGGATCTACGAGATGCTGAACACCGTGAACGAGATCTACCTG 720
               || || || || || || ||||| || || ||||| ||||| || || ||||| ||| |
WT ecarin  1   TCAACTGCTATAAGAACATGGATATATGAAATGCTCAACACTGTAAATGAGATATACTTA 720

AZ ecarin  1   CCCTTCAACATCAGAGTGGCCCTGGTGGGCCTGGAGTTCTGGTGTAACGGCGACCTGATC 780
               || ||||| ||   | || || ||||| ||||| || || ||||| || || ||| ||||
WT ecarin  1   CCTTTCAATATTCGTGTAGCACTGGTTGGCCTAGAATTTTGGTGCAATGGAGACTTGATT 780

AZ ecarin  1   AACGTGACCAGCACCGCCGACGACACCCTGCACAGCTTCGGCGAGTGGAGAGCCAGCGAC 840
               ||||||||    ||| || || || ||   ||||| || ||   ||||||||||||    ||
WT ecarin  1   AACGTGACATCCACAGCAGATGATACTTTGCACTCATTTGGAGAATGGAGAGCATCAGAT 840

AZ ecarin  1   CTGCTGAACCGGAAGAGACACGATCACGCCCAGCTGCTGACCAATGTGACCCTGGACCAC 900
               |||||||| || || ||||| ||||| || ||| | || || || ||||| ||||| ||
WT ecarin  1   TTGCTGAATCGAAAAAGACATGATCATGCTCAGTTACTCACGAACGTGACACTGGATCAT 900

AZ ecarin  1   TCCACCCTGGGCATCACCTTCGTGTACGGCATGTGTAAGAGCGACCGGAGCGTGGAGCTG 960
               |||| || || |||||| |||||||| |||||| |||||||| ||    || ||   || ||
WT ecarin  1   TCCACTCTTGGAATCACGTTCGTATATGGCATGTGCAAATCAGATCGTTCTGTAGAACTT 960

AZ ecarin  1   ATCCTGGACTACAGCAACATCACCTTCAACATGGCCTACATCATCGCCCACGAGATGGGC 1020
               || ||||| ||||||||| || || || || ||||| || || || ||||| ||||||||
WT ecarin  1   ATTCTGGATTACAGCAACATAACTTTTAATATGGCATATATAATAGCCCATGAGATGGGT 1020

AZ ecarin  21  CACAGCCTGGGCATGCTGCACGACACCAAGTTCTGTACCTGTGGCGCCAAGCCCTGTATC 1080
               || || ||||||||||| || || |||||| |||||||| ||||| || || || || ||
WT ecarin  21  CATAGTCTGGGCATGTTACATGACACAAAAATTCTGTACTTGTGGGGCTAAACCATGCATT 1080

AZ ecarin  81  ATGTTCGGCAAGGAGAGCATCCCTCCCCCTAAGGAGTTCAGCAGCTGCTCCTACGACCAG 1140
               ||||| ||||| || ||||| || || || || ||||||||| ||    || ||||||
WT ecarin  81  ATGTTTGGCAAAGAAAGCATTCCACCGCCCAAAGAATTCAGCAGTTGTAGTTATGACCAG 1140

AZ ecarin  41  TACAATAAGTACCTGCTGAAGTACAACCCCAAGTGTATCCTGGAnnnnnnnnnTGAGAAAG 1200
               || || ||||| || || || || || || || ||  || || ||         ||||||||
WT ecarin  41  TATAACAAGTATCTTCTTAAATATAACCCAAAATGCATTCTTGATCCACCTTTGAGAAAA 1200
```

FIG. 4B

```
AZ ecarin   01 GACATCGCCAGCCCTGCCGTGTGTGGCAATGAGATCTGGGAGGAGGGCGAGGAGTGTGAC 1260
               II II II    IIIII II IIIII IIIII II IIIIIIII II II II IIIII
WT ecarin   01 GATATTGCTTCACCTGCAGTTTGTGGAAATGAAATTTGGGAGGAAGGAGAAGAATGTGAT 1260

AZ ecarin   61 TGTGGCAGCCCAGCCGACTGTAGAAACCCCTGCTGTGATGCCGCCACCTGTAAGCTGAAG 1320
               IIIII      II II II III IIII II IIIIIIIIIII II II IIIII IIIII
WT ecarin   61 TGTGGTTCTCCTGCAGATTGTCGAAATCCATGCTGTGATGCTGCAACATGTAAACTGAAA 1320

AZ ecarin   21 CCTGGCGCCGAGTGTGGCAACGGCGAGTGCTGTGACAAGTGTAAGATCCGGAAGGCCGGC 1380
               II II II II IIIII II II IIIII IIIIIIIIII IIIII  IIII II II
WT ecarin   21 CCAGGGGCAGAATGTGGAAATGGAGAGTGTTGTGACAAGTGCAAGATTAGGAAAGCAGGA 1380

AZ ecarin   81 ACCGAGTGTAGACCCGCCAGGGACGATTGTGACGTGGCCGAGCACTGTACCGGCCAGAGC 1440
               II II II   I II II IIIII II IIIII II II II IIIII II IIIII
WT ecarin   81 ACAGAATGCCGGCCAGCAAGGGATGACTGTGATGTCGCTGAACACTGCACTGGCCAATCT 1440

AZ ecarin   41 GCCGAGTGCCCCAGAAACGAGTTCCAGAGGAACGGCCAGCCTTGCCTGAACAACAGCGGC 1500
               II IIIII IIIIIIIII IIIIIIII IIIII II II II IIIII IIIIII   II
WT ecarin   41 GCTGAGTGTCCCAGAAATGAGTTCCAAAGGAATGGACAACCATGCCTTAACAACTCGGGT 1500

AZ ecarin   01 TACTGCTACAACGGCGACTGCCCCATCATGCTGAACCAGTGTATCGCCCTGTTCAGCCCC 1560
               II IIIIIIII II II IIIIIIIIIII I IIIII IIIII II II II IIIII
WT ecarin   01 TATTGCTACAATGGGGATTGCCCCATCATGTTAAACCAATGTATTGCTCTCTTTAGTCCA 1560

AZ ecarin   61 AGCGCCACCGTGGCCCAGGACAGCTGCTTCCAGAGAAACCTGCAGGGCAGCTACTACGGC 1620
               II II II IIIII II II    II II IIIII III IIII IIIII IIIII III
WT ecarin   61 AGTGCAACTGTGGCTCAAGATTCATGTTTTCAGAGGAACTTGCAAGGCAGTTACTATGGC 1620

AZ ecarin   21 TACTGTACCAAGGAGATCGGCTACTACGGAAAGAGGTTCCCCTGTGCCCCTCAGGACGTG 1680
               IIIII II IIIII II II IIIII II II IIIII II IIIII II II II II
WT ecarin   21 TACTGCACAAAGGAAATTGGTTACTATGGTAAAAGGTTTCCATGTGCACCACAAGATGTA 1680

AZ ecarin   81 AAGTGTGGCAGGCTGTACTGCCTGGACAACTCCTTCAAGAAAAACATGAGGTGTAAGAAC 1740
               II IIIIIIII  I IIIIII I II II II IIIII IIIII III I II IIIIII
WT ecarin   81 AAATGTGGCAGATTATACTGCTTAGATAATTCATTCAAAAAAAATATGCGTTGCAAGAAC 1740

AZ ecarin   41 GACTACAGCTACGCCGACGAGAACAAGGGCATCGTGGAGCCCGGCACCAAGTGTGAGGAC 1800
               IIIII      IIIII II II II IIIII II II II II II II II IIIII II
WT ecarin   41 GACTATTCATACGCGGATGAAAATAAGGGAATAGTTGAACCTGGAACAAAATGTGAAGAT 1800

AZ ecarin   01 GGCAAAGTGTGTATCAACCGGAAGTGTGTGGACGTGAACACCGCCTAC 1848
               II II II II IIIIIII IIIIIIIIII II IIIII II IIIIIII
WT ecarin   01 GGAAAGGTCTGCATCAACAGGAAGTGTGTTGATGTGAATACAGCCTAC 1848
```

FIG. 4C

>◻ gi|717090|dbj|D32212.1|EHCEC  Echis carinatus mRNA for ecarin  Length = 2349
Score = 1315 bits (3404), Expect = 0.0, Identities = 616/616 (100%),
Positives = 616/616 (100%), Gaps = 0/616 (0%), Frame = +3

```
AZ ecarin    1   MIQILLVIICLAVFPYQGCSIILGSGNVNDYEVVYPQKVTALPKGAVQQPEQKYEDAMQY  60
                 MIQILLVIICLAVFPYQGCSIILGSGNVNDYEVVYPQKVTALPKGAVQQPEQKYEDAMQY
WT ecarin  111   MIQILLVIICLAVFPYQGCSIILGSGNVNDYEVVYPQKVTALPKGAVQQPEQKYEDAMQY 290

AZ ecarin   61   EFEVKGEPVVLHLEKNKELFSEDYSETHYSSDDREITTNPSVEDHCYYHGRIQNDAESTA 120
                 EFEVKGEPVVLHLEKNKELFSEDYSETHYSSDDREITTNPSVEDHCYYHGRIQNDAESTA
WT ecarin  291   EFEVKGEPVVLHLEKNKELFSEDYSETHYSSDDREITTNPSVEDHCYYHGRIQNDAESTA 470

AZ ecarin  121   SISACNGLKGHFKLRGETYFIEPLKIPDSEAHAVYKYENIENEDEAPKMCGVTQDNWESD 180
                 SISACNGLKGHFKLRGETYFIEPLKIPDSEAHAVYKYENIENEDEAPKMCGVTQDNWESD
WT ecarin  471   SISACNGLKGHFKLRGETYFIEPLKIPDSEAHAVYKYENIENEDEAPKMCGVTQDNWESD 650

AZ ecarin  181   EPIKKTLGLIVPPHERKFEKKFIELVVVVDHSMVTKYNNDSTAIRTWIYEMLNTVNEIYL 240
                 EPIKKTLGLIVPPHERKFEKKFIELVVVVDHSMVTKYNNDSTAIRTWIYEMLNTVNEIYL
WT ecarin  651   EPIKKTLGLIVPPHERKFEKKFIELVVVVDHSMVTKYNNDSTAIRTWIYEMLNTVNEIYL 830

AZ ecarin  241   PFNIRVALVGLEFWCNGDLINVTSTADDTLHSFGEWRASDLLNRKRHDHAQLLTNVTLDH 300
                 PFNIRVALVGLEFWCNGDLINVTSTADDTLHSFGEWRASDLLNRKRHDHAQLLTNVTLDH
WT ecarin  831   PFNIRVALVGLEFWCNGDLINVTSTADDTLHSFGEWRASDLLNRKRHDHAQLLTNVTLDH 1010

AZ ecarin  301   STLGITFVYGMCKSDRSVELILDYSNITFNMAYIIAHEMGHSLGMLHDTKFCTCGAKPCI 360
                 STLGITFVYGMCKSDRSVELILDYSNITFNMAYIIAHEMGHSLGMLHDTKFCTCGAKPCI
WT ecarin 1011   STLGITFVYGMCKSDRSVELILDYSNITFNMAYIIAHEMGHSLGMLHDTKFCTCGAKPCI 1190

AZ ecarin  361   MFGKESIPPPKEFSSCSYDQYNKYLLKYNPKCILDPPLRKDIASPAVCGNEIWEEGEECD 420
                 MFGKESIPPPKEFSSCSYDQYNKYLLKYNPKCILDPPLRKDIASPAVCGNEIWEEGEECD
WT ecarin 1191   MFGKESIPPPKEFSSCSYDQYNKYLLKYNPKCILDPPLRKDIASPAVCGNEIWEEGEECD 1370

AZ ecarin  421   CGSPADCRNPCCDAATCKLKPGAECGNGECCDKCKIRKAGTECRPARDDCDVAEHCTGQS 480
                 CGSPADCRNPCCDAATCKLKPGAECGNGECCDKCKIRKAGTECRPARDDCDVAEHCTGQS
WT ecarin 1371   CGSPADCRNPCCDAATCKLKPGAECGNGECCDKCKIRKAGTECRPARDDCDVAEHCTGQS 1550

AZ ecarin  481   AECPRNEFQRNGQPCLNNSGYCYNGDCPIMLNQCIALFSPSATVAQDSCFQRNLQGSYYG 540
                 AECPRNEFQRNGQPCLNNSGYCYNGDCPIMLNQCIALFSPSATVAQDSCFQRNLQGSYYG
WT ecarin 1551   AECPRNEFQRNGQPCLNNSGYCYNGDCPIMLNQCIALFSPSATVAQDSCFQRNLQGSYYG 1730

AZ ecarin  541   YCTKEIGYYGKRFPCAPQDVKCGRLYCLDNSFKKNMRCKNDYSYADENKGIVEPGTKCED 600
                 YCTKEIGYYGKRFPCAPQDVKCGRLYCLDNSFKKNMRCKNDYSYADENKGIVEPGTKCED
WT ecarin 1731   YCTKEIGYYGKRFPCAPQDVKCGRLYCLDNSFKKNMRCKNDYSYADENKGIVEPGTKCED 1910

AZ ecarin  601   GKVCINRKCVDVNTAY 616
                 GKVCINRKCVDVNTAY
WT ecarin 1911   GKVCINRKCVDVNTAY 1958
```

FIG. 5

SEQUENCE LISTING

<160> NUMBER OF SEQ ID NOS: 5

<210> SEQ ID NO 1
<211> LENGTH: 10139
<212> TYPE: DNA
<213> ORGANISM: Artificial Sequence
<220> FEATURE:
<223> OTHER INFORMATION: Synthetic construct

<400> SEQUENCE: 1

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
```

-continued

| | |
|---|---|
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttggta ccgagctcgg atccactagt ccagtgtggt ggaattgccc | 960 |
| ttattcctca gtgacccagg agctgacaca ctatggcgca cgtccgaggc ttgcagctgc | 1020 |
| ctggctgcct ggccctggct gccctgtgta gccttgtgca cagccagcat gtgttcctgg | 1080 |
| ctcctcagca agcacggtcg ctgctccagc gggtccggcg agccaacacc ttcttggagg | 1140 |
| aggtgcgcaa gggcaacctg gagcgagagt gcgtggagga cgtgcagc tacgaggagg | 1200 |
| ccttcgaggc tctggagtcc tccacggcta cggatgtgtt ctgggccaag tacacagctt | 1260 |
| gtgagacagc gaggacgcct cgagataagc ttgctgcatg tctggaaggt aactgtgctg | 1320 |
| agggtctggg tacgaactac cgagggcatg tgaacatcac ccggtcaggc attgagtgcc | 1380 |
| agctatggag gagtcgctac ccacataagc ctgaaatcaa ctccactacc catcctgggg | 1440 |
| ccgacctaca ggagaatttc tgccgcaacc ccgacagcag caccacggga ccctggtgct | 1500 |
| acactacaga ccccaccgtg aggaggcagg aatgcagcat ccctgtctgt ggccaggatc | 1560 |
| aagtcactgt agcgatgact ccacgctccg aaggctccag tgtgaatctg tcacctccat | 1620 |
| tggagcagtg tgtccctgat cggggggcagc agtaccaggg gcgcctggcg gtgaccacac | 1680 |
| atgggctccc ctgcctggcc tgggccagcg cacaggccaa ggccctgagc aagcaccagg | 1740 |
| acttcaactc agctgtgcag ctggtggaga acttctgccg caacccagac ggggatgagg | 1800 |
| agggcgtgtg gtgctatgtg gccgggaagc ctggcgactt tgggtactgc gacctcaact | 1860 |
| attgtgagga ggccgtggag gaggagacag gagatgggct ggatgaggac tcagacaggg | 1920 |
| ccatcgaagg gcgtaccgcc accagtgagt accagacttt cttcaatccg aggacctttg | 1980 |
| gctcgggaga ggcagactgt gggctgcgac ctctgttcga aagaagtcg ctggaggaca | 2040 |
| aaaccgaaag agagctcctg gaatcctaca tcgacgggcg cattgtggag ggctcggatg | 2100 |
| cagagatcgg catgtcacct tggcaggtga tgcttttccg gaagagtccc caggagctgc | 2160 |
| tgtgtggggc cagcctcatc agtgaccgct gggtcctcac cgccgcccac tgcctcctgt | 2220 |
| acccgccctg ggacaagaac ttcaccgaga atgaccttct ggtgcgcatt ggcaagcact | 2280 |
| cccgcaccag gtacgagcga acattgaaa agatatccat gttggaaaag atctacatcc | 2340 |
| accccagta caactggcgg gagaacctgg accgggacat tgccctgatg aagctgaaga | 2400 |
| agcctgttgc cttcagtgac tacattcacc ctgtgtgtct gcccgacagg gagacggcag | 2460 |
| ccagcttgct ccaggctgga tacaaggggc gggtgacagg ctgggcaac ctgaaggaga | 2520 |
| cgtggacagc caacgttggt aaggggcagc ccagtgtcct gcaggtggtg aacctgccca | 2580 |
| ttgtggagcg gccggtctgc aaggactcca cccggatccg catcactgac aacatgttct | 2640 |
| gtgctggtta caagcctgat gaagggaaac gaggggatgc ctgtgaaggt gacagtgggg | 2700 |
| gacccttttgt catgaagagc cccttaaca accgctggta tcaaatgggc atcgtctcat | 2760 |
| ggggtgaagg ctgtgaccgg gatgggaaat atggcttcta cacacatgtg ttccgcctga | 2820 |
| agaagtggat acagaaggtc attgatcagt ttggagagta aagggcaat tctgcagata | 2880 |
| tccagcacag tggcggccgc tcgagtctag agggcccgtt taaacccgct gatcagcctc | 2940 |
| gactgtgcct tctagttgcc agccatctgt tgtttgcccc tcccccgtgc cttccttgac | 3000 |

```
cctggaaggt gccactccca ctgtcctttc ctaataaaat gaggaaattg catcgcattg    3060
tctgagtagg tgtcattcta ttctgggggg tggggtgggg caggacagca agggggagga    3120
ttgggaagac aatagcaggc atgctgggga tgcggtgggc tctatggctt ctgaggcgga    3180
aagaaccagc tggggctcta gggggtatcc ccacgcgccc tgtagcggcg cattaagcgc    3240
ggcgggtgtg gtggttacgc gcagcgtgac cgctacactt gccagcgccc tagcgcccgc    3300
tcctttcgct ttcttccctt cctttctcgc cacgttcgcc ggctttcccc gtcaagctct    3360
aaatcggggg ctcccttttag ggttccgatt tagtgcttta cggcaccttc gaccccaaaa    3420
aacttgatta gggctgtgga atgtgtgtca gttagggtgt ggaaagtccc caggctcccc    3480
agcaggcaga agtatgcaaa gcatgcatct caattagtca gcaaccaggt gtggaaagtc    3540
cccaggctcc ccagcaggca gaagtatgca aagcatgcat ctcaattagt cagcaaccat    3600
agtcccgccc ctaactccgc ccatcccgcc cctaactccg cccagttccg cccattctcc    3660
gccccatggc tgactaattt ttttatttta tgcagaggcc gaggccgcct cggcctctga    3720
gctattccag aagtagtgag gaggcttttt tggaggccta ggcttttgca aaaagctctc    3780
tggctaacta gagaacccac tgcttactgg cttatcgaaa ttaatacgac tcactatagg    3840
gagacccaag ctggctagcg tttaaactta agcttggtac cgagctcgga tccactagtc    3900
cagtgtggtg gaattgccct ttccgcagag caatggcggt gtctgccggg tccgcgcgga    3960
cctcgcccag ctcagataaa gtacagaaag acaaggctga actgatctca gggcccaggc    4020
aggacagccg aatagggaaa ctcttgggtt ttgagtggac agatttgtcc agttggcgga    4080
ggctggtgac cctgctgaat cgaccaacgg accctgcaag cttagctgtc tttcgttttc    4140
tttttgggtt cttgatggtg ctagacattc cccaggagcg ggggctcagc tctctggacc    4200
ggaaatacct tgatgggctg gatgtgtgcc gcttcccctt gctggatgcc ctacgcccac    4260
tgccacttga ctggatgtat cttgtctaca ccatcatgtt tctgggggca ctgggcatga    4320
tgctgggcct gtgctaccgg ataagctgtg tgttattcct gctgccatac tggtatgtgt    4380
ttctcctgga caagacatca tggaacaacc actcctatct gtatgggttg ttggccttc    4440 agctaacatt catggatgca aaccactact ggtctgtgga cggtctgctg aatgcccata    4500
ggaggaatgc ccacgtgccc ctttggaact atgcagtgct ccgtggccag atcttcattg    4560
tgtacttcat tgcgggtgtg aaaaagctgg atgcagactg ggttgaaggc tattccatgg    4620
aatatttgtc ccggcactgg ctcttcagtc ccttcaaact gctgttgtct gaggagctga    4680
ctagcctgct ggtcgtgcac tggggtgggc tgctgcttga cctctcagct ggtttcctgc    4740
tcttttttga tgtctcaaga tccattggcc tgttctttgt gtcctacttc cactgcatga    4800
attcccagct tttcagcatt ggtatgttct cctacgtcat gctggccagc agccctctct    4860
tctgctcccc tgagtggcct cggaagctgg tgtcctactg cccccgaagg ttgcaacaac    4920 tgttgccccct caaggcagcc cctcagccca gtgtttcctg tgtgtataag aggagccggg    4980
gcaaaagtgg ccagaagcca gggctgcgcc atcagctggg agctgccttc accctgctct    5040
acctcctgga gcagctattc ctgccctatt ctcattttct cacccagggc tataacaact    5100
ggacaaatgg gctgtatggc tattcctggg acatgatggt gcactcccgc tcccaccagc    5160
acgtgaagat cacctaccgt gatggccgca ctggcgaact gggctacctt aaccctgggg    5220
tatttacaca gagtcggcga tggaaggatc atgcagacat gctgaagcaa tatgccactt    5280
gcctgagccg cctgcttccc aagtataatg tcactgagcc ccagatctac tttgatattt    5340
gggtctccat caatgaccgc ttccagcaga ggattttgga ccctcgtgtg gacatcgtgc    5400
```

| | |
|---|---|
| aggccgcttg gtcacccttt cagcgcacat cctgggtgca accactcttg atggacctgt | 5460 |
| ctccctggag ggccaagtta caggaaatca agagcagcct agacaaccac actgaggtgg | 5520 |
| tcttcattgc agatttccct ggactgcact tggagaattt tgtgagtgaa gacctgggca | 5580 |
| acactagcat ccagctgctg caggggaag tgactgtgga gcttgtggca gaacagaaga | 5640 |
| accagactct tcgagaggga gaaaaaatgc agttgcctgc tggtgagtac cataaggtgt | 5700 |
| atacgacatc acctagccct tcttgctaca tgtacgtcta tgtcaacact acagagcttg | 5760 |
| cactggagca agacctggca tatctgcaag aattaaagga aaaggtggag aatggaagtg | 5820 |
| aaacagggcc tctaccccca gagctgcagc ctctgttgga aggaagta aaaggggcc | 5880 |
| ctgagccaac acctctggtt cagacctttc ttagacgcca acaaaggctc caggagattg | 5940 |
| aacgccggcg aaatactcct ttccatgagc gattcttccg cttcttgttg cgaaagctct | 6000 |
| atgtctttcg ccgcagcttc ctgatgactt gtatctcact tcgaaatctg atattaggcc | 6060 |
| gtccttccct ggagcagctg gcccaggagg tgacttatgc aaacttgaga ccctttgagg | 6120 |
| cagttggaga actgaatccc tcaaacacgg attcttcaca ttctaatcct cctgagtcaa | 6180 |
| atcctgatcc tgtccactca gagttctgaa ggggccaga tgttggaagg gcaattcgag | 6240 |
| tctagagggc ccgccctgat agacggtttt tcgcccttg acgttggagt ccacgttctt | 6300 |
| taatagtgga ctcttgttcc aaactggaac aacactcaac cctatctcgg tctattcttt | 6360 |
| tgatttataa gggattttgc cgatttcggc ctattggtta aaaatgagc tgatttaaca | 6420 |
| aaaatttaac gcgaattaat tctgtggaat gtgtgtcagt tagggtgtgg aaagtcccca | 6480 |
| ggctccccag caggcagaag tatgcaaagc atgcatctca attagtcagc aaccaggtgt | 6540 |
| ggaaagtccc caggctcccc agcaggcaga agtatgcaaa gcatgcatct caattagtca | 6600 |
| gcaaccatag tcccgcccct aactccgccc atcccgcccc taactccgcc cagttccgcc | 6660 |
| cattctccgc cccatggctg actaatttt tttatttatg cagaggccga ggccgcctct | 6720 |
| gcctctgagc tattccagaa gtagtgagga ggcttttttg gaggcctagg cttttgcaaa | 6780 |
| aagctcccgg gagcttgtat atccattttc ggatctgatc aagagacagg atgaggatcg | 6840 |
| tttcgcatga ttgaacaaga tggattgcac gcaggttctc cggccgcttg ggtggagagg | 6900 |
| ctattcggct atgactgggc acaacagaca atcggctgct ctgatgccgc cgtgttccgg | 6960 |
| ctgtcagcgc aggggcgccc ggttcttttt gtcaagaccg acctgtccgg tgccctgaat | 7020 |
| gaactgcagg acgaggcagc gcggctatcg tggctggcca cgacgggcgt tccttgcgca | 7080 |
| gctgtgctcg acgttgtcac tgaagcggga agggactggc tgctattggg cgaagtgccg | 7140 |
| gggcaggatc tcctgtcatc tcaccttgct cctgccgaga agtatccat catggctgat | 7200 |
| gcaatgcggc ggctgcatac gcttgatccg gctacctgcc cattcgacca ccaagcgaaa | 7260 |
| catcgcatcg agcgagcacg tactcggatg gaagccggtc ttgtcgatca ggatgatctg | 7320 |
| gacgaagagc atcaggggct cgcgccagcc gaactgttcg ccaggctcaa ggcgcgcatg | 7380 |
| cccgacggcg aggatctcgt cgtgacccat ggcgatgcct gcttgccgaa tatcatggtg | 7440 |
| gaaaatggcc gcttttctgg attcatcgac tgtggccggc tgggtgtggc ggaccgctat | 7500 |
| caggacatag cgttggctac ccgtgatatt gctgaagagc ttggcggcga atgggctgac | 7560 |
| cgcttcctcg tgctttacgg tatcgccgct cccgattcgc agcgcatcgc cttctatcgc | 7620 |
| cttcttgacg agttcttctg agcgggactc tggggttcga aatgaccgac caagcgacgc | 7680 |
| ccaacctgcc atcacgagat ttcgattcca ccgccgcctt ctatgaaagg ttgggcttcg | 7740 |
| gaatcgtttt ccgggacgcc ggctggatga tcctccagcg cggggatctc atgctggagt | 7800 |

```
tcttcgccca ccccaacttg tttattgcag cttataatgg ttacaaataa agcaatagca    7860
tcacaaattt cacaaataaa gcattttttt cactgcattc tagttgtggt ttgtccaaac    7920
tcatcaatgt atcttatcat gtctgtatac cgtcgacctc tagctagagc ttggcgtaat    7980
catggtcata gctgtttcct gtgtgaaatt gttatccgct cacaattcca cacaacatac    8040
gagccggaag cataaagtgt aaagcctggg gtgcctaatg agtgagctaa ctcacattaa    8100
ttgcgttgcg ctcactgccc gctttccagt cgggaaacct gtcgtgccag ctgcattaat    8160
gaatcggcca acgcgcgggg agaggcggtt tgcgtattgg gcgctcttcc gcttcctcgc    8220
tcactgactc gctgcgctcg tcgttcggc tgcggcgagc ggtatcagct cactcaaagg    8280
cggtaatacg gttatccaca gaatcagggg ataacgcagg aaagaacatg tgagcaaaag    8340
gccagcaaaa ggccaggaac cgtaaaaagg ccgcgttgct ggcgtttttc cataggctcc    8400
gcccccctga cgagcatcac aaaaatcgac gctcaagtca gaggtggcga aacccgacag    8460
gactataaag ataccaggcg tttccccctg gaagctccct cgtgcgctct cctgttccga    8520
ccctgccgct taccggatac ctgtccgcct ttctcccttc gggaagcgtg gcgctttctc    8580
atagctcacg ctgtaggtat ctcagttcgg tgtaggtcgt tcgctccaag ctgggctgtg    8640
tgcacgaacc ccccgttcag cccgaccgct gcgccttatc cggtaactat cgtcttgagt    8700
ccaacccggt aagacacgac ttatcgccac tggcagcagc cactggtaac aggattagca    8760
gagcgaggta tgtaggcggt gctacagagt tcttgaagtg gtggcctaac tacggctaca    8820
ctagaagaac agtatttggt atctgcgctc tgctgaagcc agttaccttc ggaaaaagag    8880
ttggtagctc ttgatccggc aaacaaacca ccgctggtag cggtttttt gtttgcaagc    8940
agcagattac gcgcagaaaa aaaggatctc aagaagatcc tttgatcttt tctacggggt    9000
ctgacgctca gtggaacgaa aactcacgtt aagggatttt ggtcatgaga ttatcaaaaa    9060
ggatcttcac ctagatcctt ttaaattaaa aatgaagttt taaatcaatc taagtatat    9120
atgagtaaac ttggtctgac agttaccaat gcttaatcag tgaggcacct atctcagcga    9180
tctgtctatt tcgttcatcc atagttgcct gactccccgt cgtgtagata actacgatac    9240
gggagggctt accatctggc cccagtgctg caatgatacc gcgagaccca cgctcaccgg    9300
ctccagattt atcagcaata aaccagccag ccggaagggc cgagcgcaga agtggtcctg    9360
caactttatc cgcctccatc cagtctatta attgttgccg ggaagctaga gtaagtagtt    9420
cgccagttaa tagtttgcgc aacgttgttg ccattgctac aggcatcgtg gtgtcacgct    9480
cgtcgtttgg tatggcttca ttcagctccg gttcccaacg atcaaggcga gttacatgat    9540
cccccatgtt gtgcaaaaaa gcggttagct ccttcggtcc tccgatcgtt gtcagaagta    9600
agttggccgc agtgttatca ctcatggtta tggcagcact gcataattct cttactgtca    9660
tgccatccgt aagatgcttt tctgtgactg gtgagtactc aaccaagtca ttctgagaat    9720
agtgtatgcg gcgaccgagt tgctcttgcc cggcgtcaat acgggataat accgcgccac    9780
atagcagaac tttaaaagtg ctcatcattg gaaaacgttc ttcggggcga aaactctcaa    9840
ggatcttacc gctgttgaga tccagttcga tgtaacccac tcgtgcaccc aactgatctt    9900
cagcatcttt tactttcacc agcgtttctg ggtgagcaaa aacaggaagg caaaatgccg    9960
caaaaaaggg aataagggcg acacggaaat gttgaatact catactcttc cttttttcaat   10020
attattgaag catttatcag ggttattgtc tcatgagcgg atacatattt gaatgtattt   10080
agaaaaataa acaaataggg gttccgcgca catttccccg aaaagtgcca cctgacgtc    10139
```

<210> SEQ ID NO 2

<211> LENGTH: 1851
<212> TYPE: DNA
<213> ORGANISM: Artificial Sequence
<220> FEATURE:
<223> OTHER INFORMATION: Synthetically generated oligonucleotide

<400> SEQUENCE: 2

```
atgatccaga tcctgctggt gatcatctgc ctggccgtgt cccctacca gggctgctcc      60
atcatcctgg gcagcggcaa cgtgaacgac tacgaggtgg tgtaccccca gaaggtgacc     120
gccctgccca agggcgccgt gcagcagccc gagcagaaat acgaggacgc catgcagtac     180
gagttcgagg tgaagggcga gcccgtggtg ctgcacctgg agaagaacaa ggagctgttc     240
agcgaggact acagcgagac ccactacagc agcgacgaca gggagatcac caccaacccc     300
agcgtggagg accactgcta ctaccacggc cggatccaga cgacgccga gagcaccgcc      360
agcatcagcg cctgtaatgg cctgaagggc cacttcaagc tgagaggcga gacctacttc     420
atcgagcccc tgaagatccc cgacagcgag gcccacgccg tgtacaagta cgagaacatc     480
gagaacgagg acgaggcccc taagatgtgt ggcgtgaccc aggacaactg ggagagcgac     540
gagcccatca gaaaaccct gggcctgatc gtgcccccc acgagagaaa gttcgagaag      600
aagttcatcg aactggtggt cgtggtggac cacagcatgg tgaccaagta caacaacgac     660
agcaccgcca tcaggacctg gatctacgag atgctgaaca ccgtgaacga gatctacctg     720
cccttcaaca tcagagtggc cctggtgggc ctggagttct ggtgtaacgg cgacctgatc     780
aacgtgacca gcaccgccga cgacaccctg cacagcttcg gcgagtggag agccagcgac     840
ctgctgaacc ggaagagaca cgatcacgcc cagctgctga ccaatgtgac cctggaccac     900
tccaccctgg gcatcacctt cgtgtacggc atgtgtaaga gcgaccggag cgtggagctg     960
atcctggact acagcaacat caccttcaac atggcctaca tcatcgccca cgagatgggc    1020
cacagcctgg gcatgctgca cgacaccaag ttctgtacct gtggcgccaa gccctgtatc    1080
atgttcggca aggagagcat ccctccccct aaggagttca gcagctgctc ctacgaccag    1140
tacaataagt acctgctgaa gtacaacccc aagtgtatcc tggacccccc cctgagaaag    1200
gacatcgcca gccctgccgt gtgtggcaat gagatctggg aggagggcga ggagtgtgac    1260
tgtggcagcc cagccgactg tagaaacccc tgctgtgatg ccgccacctg taagctgaag    1320
cctggcgccg agtgtggcaa cggcgagtgc tgtgacaagt gtaagatccg gaaggccggc    1380
accgagtgta gacccgccag ggacgattgt gacgtggccg agcactgtac cggccagagc    1440
gccgagtgcc ccagaaacga gttcagagg aacggccagc cttgcctgaa caacagcggc    1500
tactgctaca cggcgactg cccccatcatg ctgaaccagt gtatcgccct gttcagcccc    1560
agcgccaccg tggcccagga cagctgcttc cagagaaacc tgcagggcag ctactacggc    1620
tactgtacca aggagatcgg ctactacgga aagaggttcc cctgtgcccc tcaggacgtg    1680
aagtgtggca ggctgtactg cctggacaac tccttcaaga aaaacatgag gtgtaagaac    1740
gactacagct acgccgacga gaacaagggc atcgtggagc ccggcaccaa gtgtgaggac    1800
ggcaaagtgt gtatcaaccg gaagtgtgtg gacgtgaaca ccgcctactg a             1851
```

<210> SEQ ID NO 3
<211> LENGTH: 7280
<212> TYPE: DNA
<213> ORGANISM: Artificial Sequence
<220> FEATURE:
<223> OTHER INFORMATION: Synthetic construct

<400> SEQUENCE: 3

```
gacggatcgg gagatctccc gatccctat ggtcgactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacgggtc attagttcat agcccatata    300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaactt aagcttggta ccgagctcgg atccactagt ccagtgtggt ggaattctgc   960
agatatccac catgatccag atcctgctgg tgatcatctg cctggccgtg ttcccctacc  1020
agggctgctc catcatcctg gcagcggca acgtgaacga ctacgaggtg gtgtacccccc  1080
agaaggtgac cgccctgccc aagggcgccg tgcagcagcc cgagcagaaa tacgaggacg  1140
ccatgcagta cgagttcgag gtgaagggcg agcccgtggt gctgcacctg gagaagaaca  1200
aggagctgtt cagcgaggac tacagcgaga cccactacag cagcgacgac agggagatca  1260
ccaccaaccc cagcgtggag gaccactgct actaccacgg ccggatccag aacgacgccg  1320
agagcaccgc cagcatcagc gcctgtaatg gcctgaaggg ccacttcaag ctgagaggcg  1380
agacctactt catcgagccc ctgaagatcc ccgacagcga ggcccacgcc gtgtacaagt  1440
acgagaacat cgagaacgag gacgaggccc ctaagatgtg tggcgtgacc caggacaact  1500
gggagagcga cgagcccatc aagaaaaccc tgggcctgat cgtgcccccc cacgagagaa  1560
agttcgagaa gaagttcatc gaactggtgg tcgtggtgga ccacagcatg gtgaccaagt  1620
acaacaacga cagcaccgcc atcaggacct ggatctacga gatgctgaac accgtgaacg  1680
agatctacct gccccttcaac atcagagtgg ccctggtggg cctggagttc tggtgtaacg  1740
gcgacctgat caacgtgacc agcaccgccg acgacaccct gcacagcttc ggcgagtgga  1800
gagccagcga cctgctgaac cggaagagac acgatcacgc ccagctgctg accaatgtga  1860
ccctggacca ctccacccctg ggcatcacct tcgtgtacgg catgtgtaag agcgaccgga  1920
gcgtggagct gatcctggac tacagcaaca tcaccttcaa catggcctac atcatcgccc  1980
acgagatggg ccacagcctg ggcatgctgc acgacaccaa gttctgtacc tgtggcgcca  2040
agccctgtat catgttcggc aaggagagca tccctccccc taaggagttc agcagctgct  2100
cctacgacca gtacaataag tacctgctga agtacaaccc caagtgtatc ctggaccccc  2160
ccctgagaaa ggacatcgcc agccctgccg tgtgtggcaa tgagatctgg gagggggcg   2220
aggagtgtga ctgtggcagc ccagccgact gtagaaaccc ctgctgtgat gccgccacct  2280
gtaagctgaa gcctggcgcc gagtgtggca acggcgagtg ctgtgacaag tgtaagatcc  2340
ggaaggccgg caccgagtgt agacccgcca gggacgattg tgacgtggcc gagcactgta  2400
```

```
ccggccagag cgccgagtgc cccagaaacg agttccagag gaacggccag ccttgcctga    2460
acaacagcgg ctactgctac aacggcgact gccccatcat gctgaaccag tgtatcgccc    2520
tgttcagccc cagcgccacc gtggcccagg acagctgctt ccagagaaac ctgcagggca    2580
gctactacgg ctactgtacc aaggagatcg gctactacgg aaagaggttc ccctgtgccc    2640
ctcaggacgt gaagtgtggc aggctgtact gcctggacaa ctccttcaag aaaaacatga    2700
ggtgtaagaa cgactacagc tacgccgacg agaacaaggg catcgtggag cccggcacca    2760
agtgtgagga cggcaaagtg tgtatcaacc ggaagtgtgt ggacgtgaac accgcctact    2820
gatgagcggc cgctcgagtc tagagggccc gtttaaaccc gctgatcagc ctcgactgtg    2880
ccttctagtt gccagccatc tgttgtttgc cctcccccg tgccttcctt gaccctggaa     2940
ggtgccactc ccactgtcct ttcctaataa aatgaggaaa ttgcatcgca ttgtctgagt    3000
aggtgtcatt ctattctggg gggtggggtg gggcaggaca gcaaggggga ggattgggaa    3060
gacaatagca ggcatgctgg ggatgcggtg ggctctatgg cttctgaggc ggaaagaacc    3120
agctggggct ctagggggta tccccacgcg ccctgtagcg gcgcattaag cgcggcgggt    3180
gtggtggtta cgcgcagcgt gaccgctaca cttgccagcg ccctagcgcc cgctcctttc    3240
gctttcttcc cttcctttct cgccacgttc gccggctttc cccgtcaagc tctaaatcgg    3300
ggcatccctt tagggttccg atttagtgct ttacggcacc tcgaccccaa aaaacttgat    3360
tagggtgatg gttcacgtag tgggccatcg cccctgataga cggttttcg ccctttgacg     3420 ttggagtcca cgttctttaa tagtggactc ttgttccaaa ctggaacaac actcaaccct    3480
atctcggtct attcttttga tttataaggg attttgggga tttcggccta ttggttaaaa    3540
aatgagctga tttaacaaaa atttaacgcg aattaattct gtggaatgtg tgtcagttag    3600
ggtgtggaaa gtccccaggc tccccaggca ggcagaagta tgcaaagcat gcatctcaat    3660
tagtcagcaa ccaggtgtgg aaagtcccca ggctccccag caggcagaag tatgcaaagc    3720
atgcatctca attagtcagc aaccatagtc ccgcccctaa ctccgcccat cccgccccta    3780
actccgccca gttccgccca ttctccgccc catggctgac taattttttt tatttatgca    3840
gaggccgagg ccgcctctgc ctctgagcta ttccagaagt agtgaggagg cttttttgga    3900
ggcctaggct tttgcaaaaa gctcccggga gcttgtatat ccattttcgg atctgatcaa    3960
gagacaggat gaggatcgtt tcgcatgatt gaacaagatg gattgcacgc aggttctccg    4020
gccgcttggg tggagaggct attcggctat gactgggcac aacagacaat cggctgctct    4080
gatgccgccg tgttccggct gtcagcgcag gggcgcccgg ttcttttgt caagaccgac     4140 ctgtccggtg ccctgaatga actgcaggac gaggcagcgc ggctatcgtg gctggccacg    4200
acgggcgttc cttgcgcagc tgtgctcgac gttgtcactg aagcgggaag gactggctg     4260 ctattgggcg aagtgccggg gcaggatctc ctgtcatctc accttgctcc tgccgagaaa    4320
gtatccatca tggctgatgc aatgcggcgg ctgcatacgc ttgatccggc tacctgccca    4380
ttcgaccacc aagcgaaaca tcgcatcgag cgagcacgta ctcggatgga agccggtctt    4440
gtcgatcagg atgatctgga cgaagagcat caggggctcg cgccagccga actgttcgcc    4500
aggctcaagg cgcgcatgcc cgacggcgag gatctcgtcg tgacccatgg cgatgcctgc    4560
ttgccgaata tcatggtgga aaatggccgc ttttctggat tcatcgactg tggccggctg    4620
ggtgtggcgg accgctatca ggacatagcg ttggctaccc gtgatattgc tgaagagctt    4680
ggcggcgaat gggctgaccg cttcctcgtg ctttacggta tcgccgctcc cgattcgcag    4740
cgcatcgcct tctatcgcct tcttgacgag ttcttctgag cgggactctg gggttcgaaa    4800
```

```
tgaccgacca agcgacgccc aacctgccat cacgagattt cgattccacc gccgccttct    4860
atgaaaggtt gggcttcgga atcgttttcc gggacgccgg ctggatgatc ctccagcgcg    4920
gggatctcat gctggagttc ttcgcccacc ccaacttgtt tattgcagct tataatggtt    4980
acaaataaag caatagcatc acaaatttca caaataaagc attttttcca ctgcattcta    5040
gttgtggttt gtccaaactc atcaatgtat cttatcatgt ctgtataccg tcgacctcta    5100
gctagagctt ggcgtaatca tggtcatagc tgtttcctgt gtgaaattgt tatccgctca    5160
caattccaca acatacga gccggaagca taaagtgtaa agcctggggt gcctaatgag    5220
tgagctaact cacattaatt gcgttgcgct cactgcccgc tttccagtcg ggaaacctgt    5280
cgtgccagct gcattaatga atcggccaac gcgcgggag aggcggtttg cgtattgggc    5340
gctcttccgc ttcctcgctc actgactcgc tgcgctcggt cgttcggctg cggcgagcgg    5400
tatcagctca ctcaaaggcg gtaatacggt tatccacaga atcagggat aacgcaggaa    5460 agaacatgtg agcaaaaggc cagcaaaagg ccaggaaccg taaaaaggcc gcgttgctgg    5520 cgttttttcca taggctccgc cccctgacg agcatcacaa aaatcgacgc tcaagtcaga    5580
ggtggcgaaa cccgacagga ctataaagat accaggcgtt tccccctgga agctccctcg    5640
tgcgctctcc tgttccgacc ctgccgctta ccggatacct gtccgccttt ctcccttcgg    5700
gaagcgtggc gctttctcaa tgctcacgct gtaggtatct cagttcggtg taggtcgttc    5760
gctccaagct gggctgtgtg cacgaacccc ccgttcagcc cgaccgctgc gccttatccg    5820
gtaactatcg tcttgagtcc aacccggtaa gacacgactt atcgccactg gcagcagcca    5880
ctggtaacag gattagcaga gcgaggtatg taggcggtgc tacagagttc ttgaagtggt    5940
ggcctaacta cggctacact agaaggacag tatttggtat ctgcgctctg ctgaagccag    6000
ttaccttcgg aaaaagagtt ggtagctctt gatccggcaa acaaaccacc gctggtagcg    6060
gtggtttttt tgtttgcaag cagcagatta cgcgcagaaa aaaaggatct caagaagatc    6120
ctttgatctt ttctacgggg tctgacgctc agtggaacga aaactcacgt taagggattt    6180
tggtcatgag attatcaaaa aggatcttca cctagatcct tttaaattaa aaatgaagtt    6240
ttaaatcaat ctaaagtata tatgagtaaa cttggtctga cagttaccaa tgcttaatca    6300
gtgaggcacc tatctcagcg atctgtctat ttcgttcatc catagttgcc tgactccccg    6360
tcgtgtagat aactacgata cgggagggct taccatctgg ccccagtgct gcaatgatac    6420
cgcgagaccc acgctcaccg gctccagatt tatcagcaat aaaccagcca gccggaaggg    6480
ccgagcgcag aagtggtcct gcaactttat ccgcctccat ccagtctatt aattgttgcc    6540
gggaagctag agtaagtagt tcgccagtta atagtttgcg caacgttgtt gccattgcta    6600
caggcatcgt ggtgtcacgc tcgtcgtttg gtatggcttc attcagctcc ggttcccaac    6660
gatcaaggcg agttacatga tcccccatgt tgtgcaaaaa agcggttagc tccttcggtc    6720
ctccgatcgt tgtcagaagt aagttggccg cagtgttatc actcatggtt atggcagcac    6780
tgcataattc tcttactgtc atgccatccg taagatgctt ttctgtgact ggtgagtact    6840
caaccaagtc attctgagaa tagtgtatgc ggcgaccgag ttgctcttgc ccggcgtcaa    6900
tacgggataa taccgcgcca catagcagaa ctttaaaagt gctcatcatt ggaaaacgtt    6960
cttcggggcg aaaactctca aggatcttac cgctgttgag atccagttcg atgtaaccca    7020
ctcgtgcacc caactgatct tcagcatctt ttactttcac cagcgtttct gggtgagcaa    7080
aaacaggaag gcaaaatgcc gcaaaaaagg aataagggc gacacggaaa tgttgaatac    7140
tcatactctt cctttttcaa tattattgaa gcatttatca gggttattgt ctcatgagcg    7200
```

-continued

| | |
|---|---|
| gatacatatt tgaatgtatt tagaaaaata aacaaatagg ggttccgcgc acatttcccc | 7260 |
| gaaaagtgcc acctgacgtc | 7280 |

<210> SEQ ID NO 4
<211> LENGTH: 1848
<212> TYPE: DNA
<213> ORGANISM: Echis carinatus

<400> SEQUENCE: 4

| | |
|---|---|
| atgatccaga ttctcttggt aattatatgc ttagcagttt ttccatatca aggttgctct | 60 |
| ataatcctgg gatctgggaa tgttaatgat tatgaagtag tgtatccaca aaaagtcact | 120 |
| gcattgccca aggagcagt tcagcagcct gagcaaaagt atgaagatgc catgcaatat | 180 |
| gaatttgaag tgaagggaga gccagtggtc cttcacctag aaaaaaataa agaactttt | 240 |
| tcagaagatt acagtgagac tcattattcg tctgatgaca gagaaattac aacaaaccct | 300 |
| tcagttgagg atcactgcta ttatcatgga cggatccaga atgatgctga gtcaactgca | 360 |
| agcatcagtg catgcaatgg tttgaaagga catttcaagc ttcgagggga gacgtacttt | 420 |
| attgaaccct tgaagattcc cgacagtgaa gcccatgcag tctacaaata tgaaaacata | 480 |
| gaaaatgagg atgaagcccc caaaatgtgt ggggtaaccc aggataattg ggaatcagat | 540 |
| gaacccatca aaaagacttt ggggttaatt gttcctcctc atgaacgaaa atttgagaaa | 600 |
| aaattcattg agcttgtcgt agttgtggac cacagtatgg tcacaaaata caacaatgat | 660 |
| tcaactgcta taagaacatg gatatatgaa atgctcaaca ctgtaaatga gatatactta | 720 |
| cctttcaata ttcgtgtagc actggttggc ctagaatttt ggtgcaatgg agacttgatt | 780 |
| aacgtgacat ccacagcaga tgatactttg cactcatttg gagaatggag agcatcagat | 840 |
| ttgctgaatc gaaaaagaca tgatcatgct cagttactca cgaacgtgac actggatcat | 900 |
| tccactcttg gaatcacgtt cgtatatggc atgtgcaaat cagatcgttc tgtagaactt | 960 |
| attctggatt acagcaacat aacttttaat atggcatata taatagccca tgagatgggt | 1020 |
| catagtctgg gcatgttaca tgacacaaaa ttctgtactt gtggggctaa accatgcatt | 1080 |
| atgtttggca agaaaagcat tccaccgccc aaagaattca gcagttgtag ttatgaccag | 1140 |
| tataacaagt atcttcttaa atataaccca aaatgcattc ttgattcacc tttgagaaaa | 1200 |
| gatattgctt cacctgcagt ttgtggaaat gaaatttggg aggaaggaga agaatgtgat | 1260 |
| tgtggttctc ctgcagattg tcgaaatcca tgctgtgatg ctgcaacatg taaactgaaa | 1320 |
| ccaggggcag aatgtggaaa tggagagtgt tgtgacaagt gcaagattag gaaagcagga | 1380 |
| acagaatgcc ggccagcaag ggatgactgt gatgtcgctg aacactgcac tggccaatct | 1440 |
| gctgagtgtc ccagaaatga gttccaaagg aatggacaac catgccttaa caactcgggt | 1500 |
| tattgctaca tggggattg ccccatcatg ttaaaccaat gtattgctct ctttagtcca | 1560 |
| agtgcaactg tggctcaaga ttcatgtttt cagaggaact gcaaggcag ttactatggc | 1620 |
| tactgcacaa aggaaattgg ttactatggt aaaaggtttc catgtgcacc acaagatgta | 1680 |
| aaatgtggca gattatactg cttagataat tcattcaaaa aaaatatgcg ttgcaagaac | 1740 |
| gactattcat acgcggatga aaataaggga atagttgaac ctggaacaaa atgtgaagat | 1800 |
| ggaaaggtct gcatcaacag gaagtgtgtt gatgtgaata cagcctac | 1848 |

<210> SEQ ID NO 5
<211> LENGTH: 616
<212> TYPE: PRT
<213> ORGANISM: Kenyan Echis carinatus
<220> FEATUR
<223> OTHER INFORMATION: ecarin derived from Kenyan Echis carinatus

<400> SEQUENCE: 5

```
Met Ile Gln Ile Leu Leu Val Ile Ile Cys Leu Ala Val Phe Pro Tyr
 1               5                  10                  15

Gln Gly Cys Ser Ile Ile Leu Gly Ser Gly Asn Val Asn Asp Tyr Glu
            20                  25                  30

Val Val Tyr Pro Gln Lys Val Thr Ala Leu Pro Lys Gly Ala Val Gln
        35                  40                  45

Gln Pro Glu Gln Lys Tyr Glu Asp Ala Met Gln Tyr Glu Phe Glu Val
    50                  55                  60

Lys Gly Glu Pro Val Val Leu His Leu Glu Lys Asn Lys Glu Leu Phe
65                  70                  75                  80

Ser Glu Asp Tyr Ser Glu Thr His Tyr Ser Ser Asp Asp Arg Glu Ile
                85                  90                  95

Thr Thr Asn Pro Ser Val Glu Asp His Cys Tyr Tyr His Gly Arg Ile
            100                 105                 110

Gln Asn Asp Ala Glu Ser Thr Ala Ser Ile Ser Ala Cys Asn Gly Leu
        115                 120                 125

Lys Gly His Phe Lys Leu Arg Gly Glu Thr Tyr Phe Ile Glu Pro Leu
    130                 135                 140

Lys Ile Pro Asp Ser Glu Ala His Ala Val Tyr Lys Tyr Glu Asn Ile
145                 150                 155                 160

Glu Asn Glu Asp Glu Ala Pro Lys Met Cys Gly Val Thr Gln Asp Asn
                165                 170                 175

Trp Glu Ser Asp Glu Pro Ile Lys Lys Thr Leu Gly Leu Ile Val Pro
            180                 185                 190

Pro His Glu Arg Lys Phe Glu Lys Lys Phe Ile Glu Leu Val Val Val
        195                 200                 205

Val Asp His Ser Met Val Thr Lys Tyr Asn Asn Asp Ser Thr Ala Ile
    210                 215                 220

Arg Thr Trp Ile Tyr Glu Met Leu Asn Thr Val Asn Glu Ile Tyr Leu
225                 230                 235                 240

Pro Phe Asn Ile Arg Val Ala Leu Val Gly Leu Glu Phe Trp Cys Asn
                245                 250                 255

Gly Asp Leu Ile Asn Val Thr Ser Thr Ala Asp Asp Thr Leu His Ser
            260                 265                 270

Phe Gly Glu Trp Arg Ala Ser Asp Leu Leu Asn Arg Lys Arg His Asp
        275                 280                 285

His Ala Gln Leu Leu Thr Asn Val Thr Leu Asp His Ser Thr Leu Gly
    290                 295                 300

Ile Thr Phe Val Tyr Gly Met Cys Lys Ser Asp Arg Ser Val Glu Leu
305                 310                 315                 320

Ile Leu Asp Tyr Ser Asn Ile Thr Phe Asn Met Ala Tyr Ile Ile Ala
                325                 330                 335

His Glu Met Gly His Ser Leu Gly Met Leu His Asp Thr Lys Phe Cys
            340                 345                 350

Thr Cys Gly Ala Lys Pro Cys Ile Met Phe Gly Lys Glu Ser Ile Pro
        355                 360                 365

Pro Pro Lys Glu Phe Ser Ser Cys Ser Tyr Asp Gln Tyr Asn Lys Tyr
    370                 375                 380

Leu Leu Lys Tyr Asn Pro Lys Cys Ile Leu Asp Pro Pro Leu Arg Lys
385                 390                 395                 400

Asp Ile Ala Ser Pro Ala Val Cys Gly Asn Glu Ile Trp Glu Glu Gly
```

-continued

```
                    405                 410                 415
Glu Glu Cys Asp Cys Gly Ser Pro Ala Asp Cys Arg Asn Pro Cys Cys
            420                 425                 430

Asp Ala Ala Thr Cys Lys Leu Lys Pro Gly Ala Glu Cys Gly Asn Gly
            435                 440                 445

Glu Cys Cys Asp Lys Cys Lys Ile Arg Lys Ala Gly Thr Glu Cys Arg
            450                 455                 460

Pro Ala Arg Asp Asp Cys Asp Val Ala Glu His Cys Thr Gly Gln Ser
465                 470                 475                 480

Ala Glu Cys Pro Arg Asn Glu Phe Gln Arg Asn Gly Gln Pro Cys Leu
            485                 490                 495

Asn Asn Ser Gly Tyr Cys Tyr Asn Gly Asp Cys Pro Ile Met Leu Asn
            500                 505                 510

Gln Cys Ile Ala Leu Phe Ser Pro Ser Ala Thr Val Ala Gln Asp Ser
            515                 520                 525

Cys Phe Gln Arg Asn Leu Gln Gly Ser Tyr Tyr Gly Tyr Cys Thr Lys
            530                 535                 540

Glu Ile Gly Tyr Tyr Gly Lys Arg Phe Pro Cys Ala Pro Gln Asp Val
545                 550                 555                 560

Lys Cys Gly Arg Leu Tyr Cys Leu Asp Asn Ser Phe Lys Lys Asn Met
            565                 570                 575

Arg Cys Lys Asn Asp Tyr Ser Tyr Ala Asp Glu Asn Lys Gly Ile Val
            580                 585                 590

Glu Pro Gly Thr Lys Cys Glu Asp Gly Lys Val Cys Ile Asn Arg Lys
            595                 600                 605

Cys Val Asp Val Asn Thr Ala Tyr
            610                 615
```

METHOD FOR PRODUCTION OF RECOMBINANT HUMAN THROMBIN

CROSS REFERENCE TO RELATED APPLICATIONS

This application claims the benefit under 35 U.S.C. §119(e) of U.S. Provisional Application No. 60/948,207 (US) filed on 6 Jul. 2007, which is incorporated herein by reference in its entirety.

TECHNICAL FIELD

The present application relates to a method for producing recombinant human thrombin from recombinant prothrombin using recombinant ecarin.

BACKGROUND OF THE INVENTION

Thrombin is a key enzyme in the coagulation cascade. By thrombin mediated proteolytic digestion of fibrinogen into fibrin monomer, a cascade reaction leading to clot formation is started. Clot formation is the first step in wound healing. In addition thrombin is a chemo attractant to cells involved in wound healing, and, the fibrin network formed act as a scaffold for collagen-producing fibroblasts, increases phagocytosis, promotes angiogenesis and binds growth factors thus further supporting the healing process. The rate of clot formation is dependent on the concentration of thrombin and fibrinogen. Because of the important function in clot formation thrombin has been utilised in a number of products intended for haemostasis and/or as tissue sealants or "glues", both as stand-alone products (i.e. Thrombin-JMI) or in combination with fibrin or other compounds (i.e. Tisseel, Hemaseel, Crosseal). The potential fields of use are numerous; skin grafting, neuro surgery, cardiac surgery, toracic surgery, vascular surgery, oncologic surgery, plastic surgery, opthalmologic surgery, orthopedic surgery, trauma surgery, head and neck surgery, gynecologic and urologic surgery, gastrointestinal surgery, dental surgery, drug delivery, tissue engineering and dental cavity haemostasis.

So far the thrombin in approved thrombin-containing products on the market is derived either from human or bovine plasma. Using plasma derived protein confers several disadvantages as limited availability and safety concerns such as risk for transmission of viruses and prions and the risk of triggering autoantibody formation (bovine products). Cases where antibody formation due to bovine thrombin exposure has lead to significant bleeding disorders are known.

In vivo thrombin is obtained from activation of prothrombin through the coagulation cascade. Activation through the coagulation cascade is dependent on the presence of a functional GLA-domain containing 8-10 glutamic residues converted to gamma-carboxyglutamate. In vitro, also incomplete gamma-carboxylated prothrombin can be converted to thrombin by the use of prothrombin activators such as ecarin. Ecarin, a snake venom derived from the Kenyan viper *Echis carinatus* is a procoagulant, a protease which cleaves human prothrombin between residues $Arg_{320}$-$Ile_{321}$ to generate meizothrombin. Further autocatalytic processing results in the formation of meizothrombin desF1 and then alpha-thrombin, which is the mature active form of thrombin.

An ideal commercial thrombin manufacturing process would use a recombinant thrombin precursor and a recombinant protease produced at high productivity without addition of animal-derived components. Further requirements would be robust performance, convenience and low cost.

A big obstacle for efficient recombinant human thrombin (rh-thrombin) has been to obtain high yields of prothrombin. Although extensive efforts have been spent, obtaining high yields of prothrombin under conditions suitable for production of biologicals has long remained a challenge. Yonemura et al. (J Biochem 135:577-582, 2004) have used recombinant GLA-domain-less prethrombin digested with recombinant ecarin to generate recombinant human thrombin. The productivity of prethrombin at process scale was 150-200 mg/L, which is a modest productivity for commercial scale production. Recombinant production of ecarin has also been described in WO 01/04146. In this publication generation of rh-thrombin is exemplified by conversion of recombinant prothrombin produced in COS cells by a recombinant ecarin produced from CHO cells. However, the exemplified methods are not suitable for large-scale production and animal-derived components are used.

Recombinant ecarin is produced as a prepro-protein that needs to be activated. Problems to efficiently activate the r-ecarin are described in both publications and the suggested activation procedures are far from optimal.

Thus there is a need for improved methods to obtain recombinant human thrombin. During our efforts to obtain improved productivity of gamma-carboxylated human prothrombin we made the surprising discovery that co-expression with gamma-glutamyl carboxylase (GGCX) vastly improved also the productivity of incompletely carboxylated prothrombin (see WO2005038019).

The present invention describes a process to efficiently produce human thrombin from recombinant prothrombin obtained by the expression method as described in WO2005038019. Recombinant carboxylated or incompletely carboxylated prothrombin combined with recombinant ecarin has not previously been used for manufacturing of recombinant thrombin. Further, the procedure for activating recombinant ecarin is new. The methods described would be suitable for large scale rh-thrombin manufacturing without the addition of animal-derived components.

SUMMARY OF THE INVENTION

According to a first aspect of the invention, a method is provided for producing recombinant human thrombin from recombinant prothrombin using recombinant ecarin having the sequence SEQ ID NO 2 or a homologue thereof.

According to a another aspect, a pharmaceutical composition is provided comprising a recombinant thrombin according to said method, in combination with pharmaceutically acceptable carriers, vehicles and/or adjuvants.

According to further aspect, an isolated DNA sequence is provided coding for recombinant ecarin according to SEQ ID NO 2 or a homologue thereof, having at least 80% identity to SEQ ID NO 2.

According to another aspect, a vector is provided comprising an isolated DNA sequence coding for recombinant ecarin according to SEQ ID NO 2 or a homologue thereof, having at least 80% identity to SEQ ID NO 2.

According to yet another aspect, a cell line is provided comprising a vector comprising an isolated DNA sequence coding for recombinant ecarin according to SEQ ID NO 2 or a homologue thereof, having at least 80% identity to SEQ ID NO 2.

BRIEF DESCRIPTION OF THE DRAWINGS

FIGS. 4A-4C. Nucleotide sequence alignment of the nucleic acid sequence encoding recombinant ecarin (SEQ ID NO:2) used in the present invention and wild type ecarin nucleic acid sequence (SEQ ID NO:4).
FIG. 5. Amino acid sequence alignment of recombinant ecarin (encoded by SEQ ID NO:2) used in the present invention and wild type ecarin (both having the amino acid sequence of SEQ ID NO:5).

DETAILED DESCRIPTION OF THE INVENTION

Figure 1:
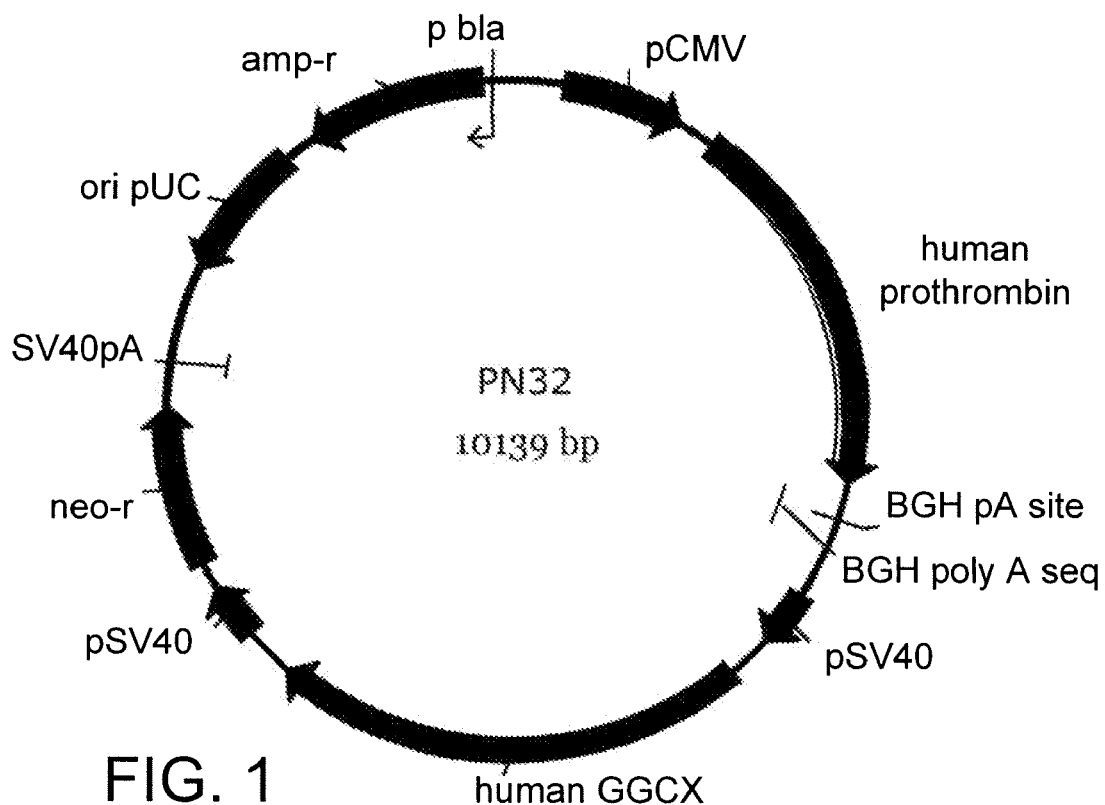
FIG. 1. FII+GGCX construct (SEQ ID NO:1).

The invention consists in one part of a cell line derived by stable transfection with a vector (FIG. 1) encoding human prothrombin (FII) associated by suitable control sequences and human gamma-glutamyl carboxylase (GGCX) associated by suitable control sequences. Control sequences should be chosen so that prothrombin expression is in excess of the GGCX expression by at least a factor of 10. The host cell is preferably a eukaryotic cell. Typical host cells include, but are not limited to insect cells, yeast cells, and mammalian cells. Mammalian cells are particularly preferred. Suitable mammalian cells lines include, but are not limited to, CHO, HEK, NS0, 293, Per C.6, BHK and COS cells, and derivatives thereof. In one embodiment the host cell is the mammalian cell line CHO-S. The obtained prothrombin producing cell line is grown under culture conditions optimised for high yield of prothrombin disregarding gamma-carboxylation. Vitamin K may or may not be added to the growth medium.

It will be appreciated that the invention is not restricted to a particular prothrombin or gamma-glutamyl carboxylase or protein encoding sequence of one of these proteins to be co-expressed. Moreover, and in particular with respect to blood coagulation factors, numerous mutant forms of the proteins have been disclosed in the art. The present invention is equally applicable to prothrombin and gamma-glutamyl carboxylase mutant forms, including naturally occurring allelic variants, of the proteins as it is to wild-type sequence. In one embodiment the invention can be undertaking with any wild-type protein or one with at least 90%, preferably at least 95% sequence identity thereto. In another embodiment, sequences listed in Table 1 can be used.

Each of these proteins, including their nucleic acid and amino acid sequences, are well known. Table 2 identifies representative sequences of wild-type and mutant forms of the various proteins that can be used in the present invention.

The term "gamma-glutamyl carboxylase" or "GGCX", as used herein, refers to a vitamin K dependent enzyme that catalyses carboxylation of glutamic acid residues.

GGCX enzymes are widely distributed, and have been cloned from many different species such as the beluga whale *Delphinapterus leucas*, the toadfish *Opsanus tau*, chicken (*Gallus gallus*), hagfish (*Myxine glutinosa*), horseshoe crab (*Limulus polyphemus*), and the cone snail *Conus textile* (Begley et al., 2000, ibid; Bandyopadhyay et al. 2002, ibid). The carboxylase from conus snail is similar to bovine carboxylase and has been expressed in COS cells (Czerwiec et al. 2002, ibid). Additional proteins similar to GGCX can be found in insects and prokaryotes such as *Anopheles gambiae*, *Drosophila melanogaster* and *Leptospira* with NCBI accession numbers: gi 31217234, gi 21298685, gi 24216281, gi 24197548 and (Bandyopadhyay et al., 2002, ibid), respectively. The carboxylase enzyme displays remarkable evolutionary conservation. Several of the non-human enzymes have shown, or may be predicted to have, activity similar to that of the human GGCX we have used, and may therefore be used as an alternative to the human enzyme.

Table 2 identifies representative sequences of predicted proteins homologous to human GGXC (sorted after species origin) that can be used in the present invention.

TABLE 2

| Species | Data base accession #/ID |
| --- | --- |
| *Homo sapiens* (man) | NM_000821.2 |
| | HUMGLUCARB |
| | HUMHGCA |
| | BC004422 |
| | HSU65896 |
| | AF253530.1 |
| *Papio hamadryas* (red baboon) | AC116665.1 |
| *Delphinapterus leucas* (white whale) | AF278713 |
| *Bos taurus* (bovine) | NM_174066.2 |
| | BOVCARBOXG |
| | BOVBGCA |
| *Ovis aries* (domestic sheep) | AF312035 |
| *Rattus norvegicus* (brown rat) | NM_031756.1 |
| | AF065387 |
| *Mus musculus* (mouse) | NM_019802.1 |
| | AF087938 |
| *Opsanus tau* (bony fishes) | AF278714.1 |
| *Conus textile* (molluscs) | AY0044904.1 |
| | AF382823.2 |
| *Conus imperialis* (molluscs) | AF448234.1 |
| *Conus episcopatus* (molluscs) | AF448233.1 |
| *Conus omaria* (molluscs) | AF448235.1 |
| *Drosophila melanogaster* (fruit fly) | NM_079161.2 |
| *Anopheles gambiae* (mosquito) | XM_316389.1 |
| *Secale cereale* (monocots) | SCE314767 |
| *Triticum aestivum* (common wheat) | AF280606.1 |
| *Triticum urartu* (monocots) | AY245579.1 |

TABLE 1

| PROTEIN | CDNA EMBL ACC# | SPLICE VARIANTS (PROTEIN) | MUTATIONS | GENE EMBL ACC# |
| --- | --- | --- | --- | --- |
| Glutamate gamma carboxylase | BC013979 | 2; BC013979; AF253530 | 1 SNP (EMBL# U65896); 2 SNPs (OMIM# 137167) | U65896 |
| Prothrombin | V00595 | 1; V00595 | approx. 100 SNP's (EMBL# AF478696) | AF478696 |

TABLE 2-continued

| Species | Data base accession #/ID |
|---|---|
| Hordeum vulgare (barley) | BLYHORDCA |
| Leptospira interrogans (spirochetes) | AE011514.1 |
| Streptomyces coelicolor (high GC Gram+ bacteria) | SCO939109 SCO939124 AF425987.1 |
| Streptomyces lividans (high GC Gram+ bacteria) | SLU22894 |
| Streptomyces viginiae (high GC Gram+ bacteria) | SVSNBDE |
| Micrococcus luteus (high GC Gram+ bacteria) | MLSPCOPER |
| Chlamydomonas reinhardtii (green algae) | AF479588.1 |
| Dictyostelium discoideum (slime mold) | AC115612.2 |
| Coturnix coturnix (birds) | AF364329.1 |
| Bradyrhizobium japonicum (α-protoebacteria) | AP005937.1 |
| Rhodobacter sphaeroides (α-proteobacteria) | RSY14197 |
| Sinorhizobium meliloti (α-proteobacteria) | RME603647 AF119834 |
| Mesorhizobium loti (α-proteobacteria) | AP003014.2 |
| Chromobacterium violaceum (β-proteobacteria) | AE016910.1 AE016918.1 |
| Pseudomonas aeruginosa (γ-proteobacteria) | AE004613.1 AF165882 |
| Xanthomonas axonopodis (γ-proteobacteria) | AE011706.1 |
| Human herpesvirus 8 | KSU52064 KSU75698 AF305694 AF360120 AF192756 |

Each of the above-identified GGCX proteins and GGCX proteins from other species can be used as the carboxylase enzyme in the present invention.

Figure 2:
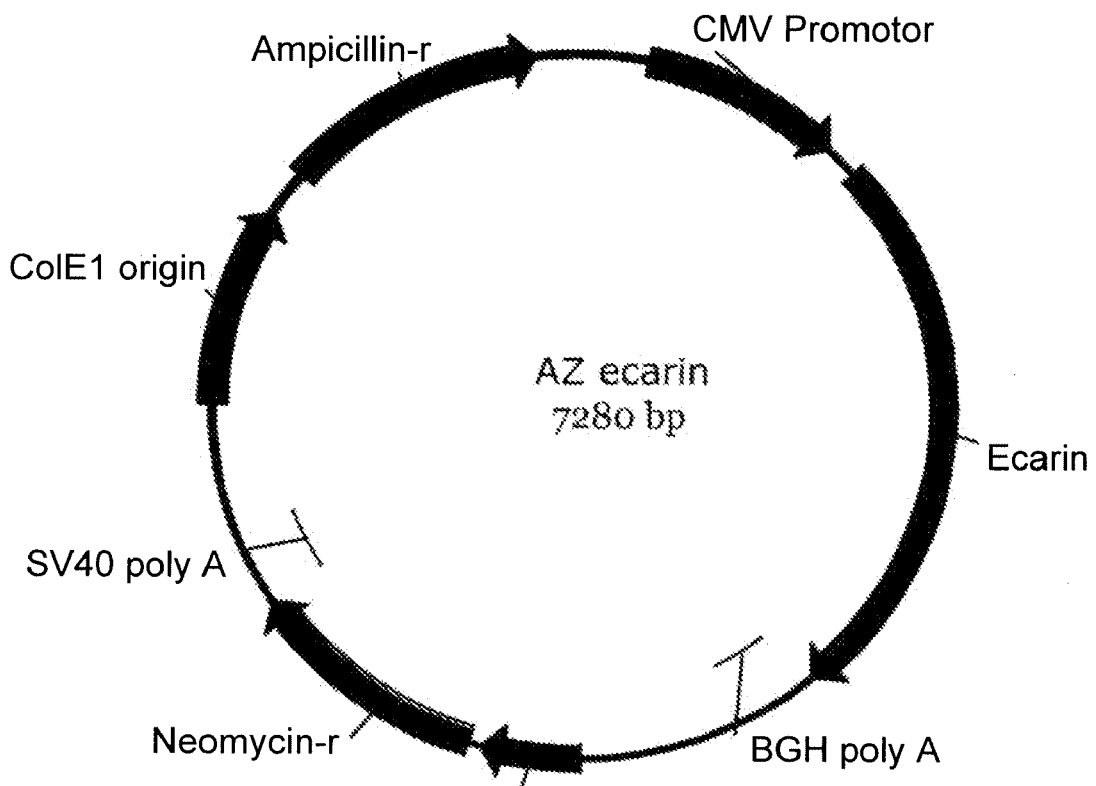
FIG. 2. Ecarin construct (SEQ ID NO:3).

A second part of the invention is a cell line stably transfected with a polynucleotide encoding ecarin and associated control elements (FIG. 2). The ecarin encoding sequence may be optimised for expression in mammalian cells, but is not limited to such sequences. In one embodiment of the invention the sequence according to SEQ ID NO 2 or a homologue thereof is used to express ecarin. A homologue of SEQ ID NO 2 coding for ecarin may have at least 80%, 85%, 90%, 95%, 97%, 98% or 99% identity to the sequence SEQ ID NO 2. The host cell is preferably a eukaryotic cell. Typical host cells include, but are not limited to insect cells, yeast cells, and mammalian cells. Mammalian cells are particularly preferred. Suitable mammalian cells lines include, but are not limited to, CHO, HEK, NS0, 293, Per C.6, BHK and COS cells, and derivatives thereof. In one embodiment the host cell is the mammalian cell line CHO-S.

In one embodiment prothrombin and ecarin are produced from cells originating from the same parent cell line. This cell line origin may be, but is not limited to, Chinese Hamster Ovary cells (CHO) including derivatives and NS0 (myeloma BALB/c mouse) including derivatives. The purpose of using the same cell line background is to facilitate purification and evaluation of purity of the thrombin product.

In another embodiment ecarin and prothrombin are produced from different host cell line; i.e. CHO and NS0, respectively.

In one aspect of the invention use of recombinant ecarin is preferred as this facilitates detection of non-thrombin product derived components during the thrombin generation process and in the final thrombin product. In a second aspect recombinant ecarin is preferred due to reduced risk for exposure to allergenic or toxic components that may be present in ecarin derived from snake venom. In a third aspect ecarin from snake venom is not preferred due to batch variation and limited batch size of ecarin preparations.

The crude prothrombin and the crude ecarin are mixed and incubated under conditions that allow formation of thrombin, such as described in Example 3. Generated thrombin is then purified by methods described in Example 4 or by other methods known by persons skilled in the art. Alternatively prothrombin and/or ecarin can first be purified by methods known in the art and then mixed to obtain thrombin. Thrombin is then purified from non-product components.

Figure 3:
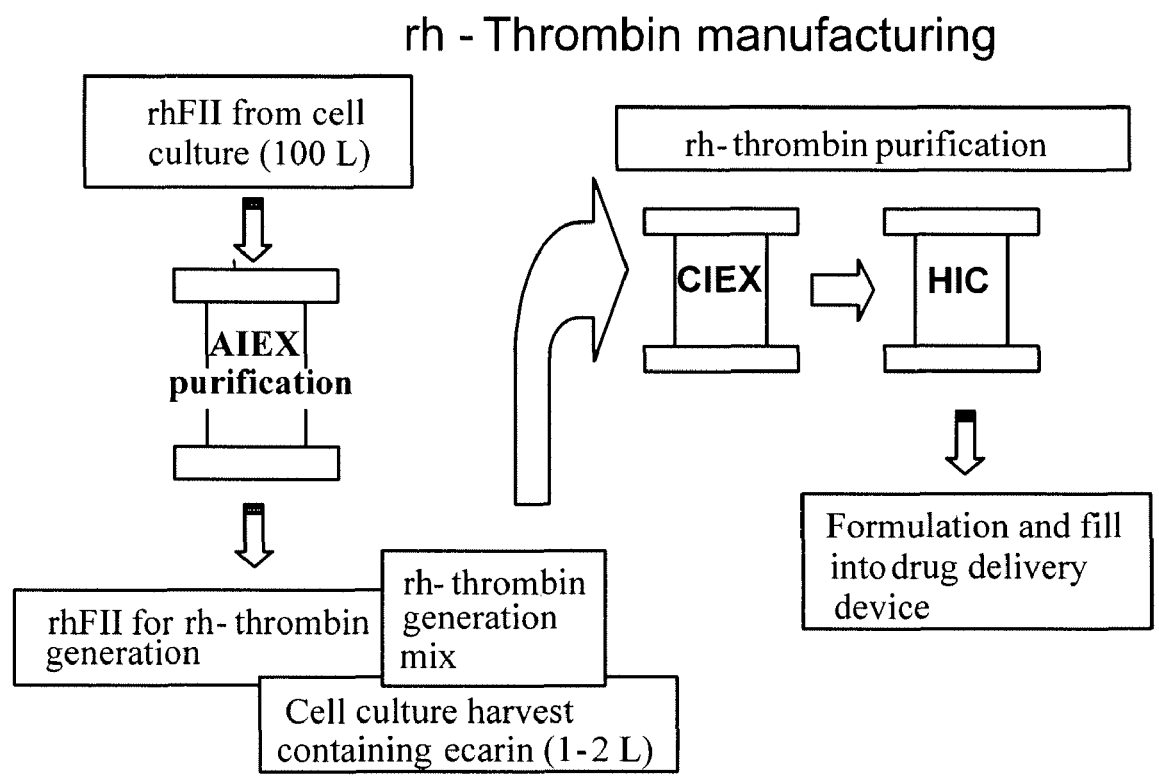
FIG. 3. Example of a process outline for thrombin manufacturing.

An example of a suitable thrombin manufacturing process is outlined in FIG. 3.

A method is provided for producing recombinant human thrombin from recombinant prothrombin using recombinant ecarin having the sequence SEQ ID NO 2 or a homologue thereof. The recombinant ecarin can be expressed and secreted by a cell containing the gene comprising the nucleotide sequence SEQ ID NO 2 or a homologue thereof in CHO-S cells, which ecarin has an amino acid sequence equal to that of wild type ecarin.

In the above method the recombinant prothrombin is subjected to recombinant ecarin, which recombinant ecarin can be isolated in active form after extra-cellular expression by CHO-S cells, said cells being left to apoptosis/necrosis for a time sufficient to activate said ecarin, whereupon a human recombinant thrombin is isolated.

The recombinant prothrombin can be produced by a cell-line comprising a prothrombin expressing gene having a nucleotide sequence comprising the sequence SEQ. ID. NO. 1 or an homologue thereof. A homologue of SEQ ID NO 1 coding for prothrombin may have at least 80%, 85%, 90%, 95%, 97%, 98% or 99% identity to the sequence SEQ ID NO 1. The recombinant prothrombin can be a mixture of fully carboxylated prothrombin and incompletely carboxylated prothrombin. In one embodiment, the recombinant prothrombin is a fully carboxylated prothrombin and in another embodiment, the recombinant prothrombin is an incompletely carboxylated prothrombin.

A further aspect of the invention relates to the recombinant thrombin obtained by the method according to the invention. A pharmaceutical composition can be designed comprising the recombinant thrombin obtained be the method according to the invention, in combination with pharmaceutically acceptable carriers, vehicles and/or adjuvants. The pharmaceutical composition can be in an applicable form.

In one embodiment thrombin produced by the described method can be used in the manufacturing of tissue sealants ("glues") in combination with other proteins, i.e. fibrin originating from recombinant cells, transgenic animals or human plasma. In another embodiment thrombin produced by the described method can be used as a stand-alone product, freeze dried as single active component or in combination with a non-protein matrix, or, in solution as single active component or in combination with other active components.

Suitable mix-in components would be, but is not limited to, collagen, chitin, degradable polymers, cellulose, recombinant coagulation factors and fibrinogen from transgenic or recombinant sources.

The potential fields of use for the tissue sealants ("glues") are numerous; skin grafting, neuro surgery, cardiac surgery, toracic surgery, vascular surgery, oncologic surgery, plastic surgery, opthalmologic surgery, orthopedic surgery, trauma surgery, head and neck surgery, gynecologic and urologic surgery, gastrointestinal surgery, dental surgery, drug delivery, tissue engineering and dental cavity haemostasis.

A further aspect of the invention relates to a method for obtaining coagulation by administering a therapeutically effective amount of a recombinant human thrombin obtained using the method according to the invention to a patient.

Another aspect of the present invention is an isolated DNA sequence according SEQ ID NO 2 or homologues thereof coding for a recombinant ecarin. A homologue of SEQ ID NO 2 coding for ecarin may have at least 80%, 85%, 90%, 95%, 97%, 98% or 99% identity to the sequence SEQ ID NO 2. SEQ ID NO 2 is a designed sequence that has been optimised for optimal expression. The sequence is particularly suited for expression in mammalian cell systems.

According to another aspect a vector comprising SEQ ID NO 2 or a homologue thereof is provided. Said vector can be designed to overexpress SEQ ID NO 2 or a homologue thereof and is operably linked to expression control sequences permitting expression of ecarin encoded by SEQ ID NO 2 or a homologue thereof. According to a third aspect a host cell comprising said vector is provided that is capable of expressing ecarin encoded by SEQ ID NO 2 or a homologue thereof. This host cell is preferably a eukaryotic cell. Typical host cells include, but are not limited to insect cells, yeast cells, and mammalian cells. Mammalian cells are particularly preferred. Suitable mammalian cells lines include, but are not limited to, CHO, HEK, NSO, 293, Per C.6, BHK and COS cells, and derivatives thereof. In one embodiment the host cell is the mammalian cell line CHO-S.

According to another embodiment of the present invention a polypeptide comprising an amino acid sequence encoded by SEQ ID NO: 2 or a homologue thereof and obtained by the method described in Example 2.

The sequence identity between two sequences can be determined by pair-wise computer alignment analysis, using programs such as, BestFit, PILEUP, Gap or FrameAlign. The preferred alignment tool is BestFit. In practise, when searching for similar/identical sequences to the query search, from within a sequence database, it is generally necessary to perform an initial identification of similar sequences using suitable algorithms such as Blast, Blast2, NCBI Blast2, WashU Blast2, FastA, or Fasta3, and a scoring matrix such as Blosum 62. Such algorithms endeavour to closely approximate the "gold-standard" alignment algorithm of Smith-Waterman. Thus, the preferred software/search engine program for use in assessing similarity, i.e., how two primary polypeptide sequences line up is Smith-Waterman. Identity refers to direct matches, similarity allows for conservative substitutions.

EXPERIMENTAL SECTION

The invention will be further described by means of the following examples which shall not be interpreted as limiting the scope of the appended claims.

Example 1

High Yield Production of Recombinant Human Prothrombin in CHO Cells

The P1E2 cell line containing the construct PN32 shown in FIG. 1 having the nucleotide sequence SEQ ID NO: 1, was grown in a fermentor according to the method described in WO2005038019, using a protein and animal component free growth medium in order to produce prothrombin for use in thrombin manufacturing. The cells were grown either by batch or perfusion culture methods (Table 1) and the amount of prothrombin produced was measured by an ecarin assay. This ecarin assay was performed essentially as the Chromogenix assay (Mölndal, Sweden) using purified plasma-derived human prothrombin (Haematologic Technologies Inc., Vermont, USA) as standard.

TABLE 1

Examples of yield of prothrombin in experimental fermentor runs

| Experiment ID | Culture method & time | Viable cells (million cells/mL) | Prothrombin mg/L |
|---|---|---|---|
| CC2LC (272-8) | Batch, 238 h | 5.9 | 281 |
| CC2LD (272-8) | Batch, 238 h | 6.2 | 276 |
| 326-11B | Perfusion, 259 h | 18 | 722 |

The fermentor experiments showed that both batch and perfusion culture methods can be used to produce prothrombin suitable for production of recombinant thrombin (Table 1). The share of fully carboxylated prothrombin obtained in these fermentor runs was about 55-87%, the rest being incompletely carboxylated prothrombin.

Example 2

Production of Recombinant Ecarin in CHO Cells

An ecarin encoding sequence having the nucleotide sequence SEQ ID NO: 2 optimised for expression in mammalian cells was synthesized and cloned into the Invitrogen vector pCDNA 3.1+ (FIG. 2). An alignment of the nucleotide sequence of the recombinant ecarin used in the present invention to the sequence of wild type ecarin (GI:717090) is seen in FIG. 4. As can be seen in FIG. 5 this recombinant ecarin is 100% homologous to the amino acid sequence for wild type ecarin. This construct, AZ ecarin (SEQ ID NO. 3), was used to stably transfect CHO-S cells (Invitrogen). Ecarin is secreted by the host cell to the extra-cellular space, and in order to screen for ecarin producing clones, culture supernatant samples were removed and mixed with recombinant human prothrombin (rhFII) to a final concentration of 1 mg rhFII/L in assay buffer (50 mM Tris-HCl, pH 7.4 containing 0.1% BSA). This mix was incubated 20-40 minutes at 37° C. The thrombin generated by the action of ecarin present in the sample was then detected by adding a 1-2 mM solution of the chromogenic thrombin substrate S-2238 (Chromogenix, Mölndal). Colour development was monitored and stopped when suitable using 20% acetic acid. To estimate the activity of the recombinant ecarin produced, snake venom derived ecarin with a declared activity was purchased from Sigma and used as standard. The best producing cell line obtained produced up to 7000 U ecarin per liter culture in lab scale shaker cultures grown in animal component free medium.

Activation of Recombinant Ecarin

Figure 6:
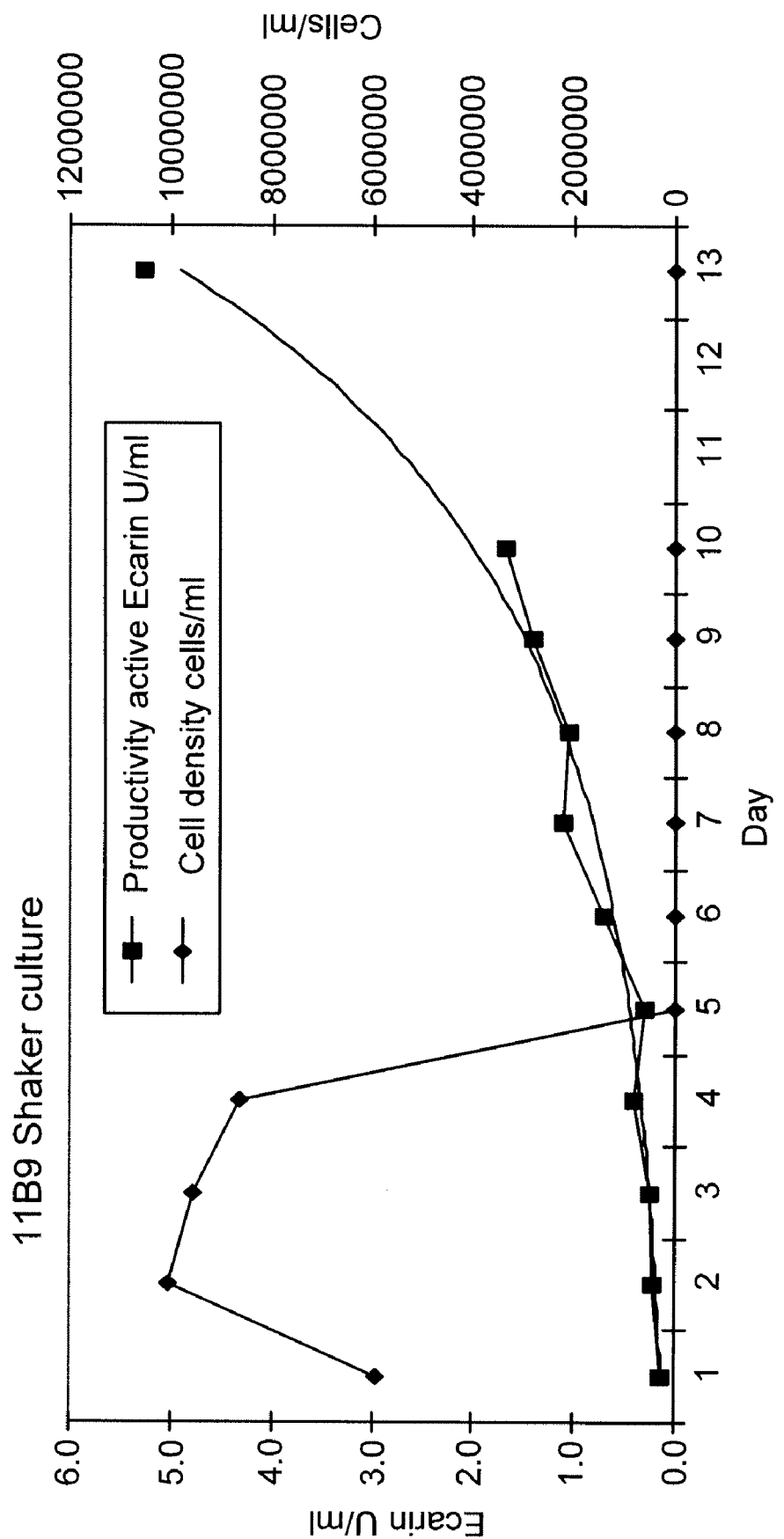
FIG. 6. Graph showing the activation of recombinant ecarin during cell death over time.

The above method produces the recombinant ecarin as a pro protein Thus, activation by removal of the pro-part is necessary for optimal activity. To our surprise, we found that activation was most conveniently obtained by continued incubation of the culture for at least 7 days after the death of the ecarin producing cells (FIG. 6). The culture medium used was CD-CHO supplemented with HT-supplement, non-essential amino acids and Glutamax I (as recommended by Invitrogen for CHO-S), and growth conditions were shaker bottles at 37° C. in an atmosphere containing 5% carbon dioxide. Culture samples were assayed for activity as described above. As can be seen from FIG. 6, the activity of recombinant ecarin increased during the activation period.

Figure 7:
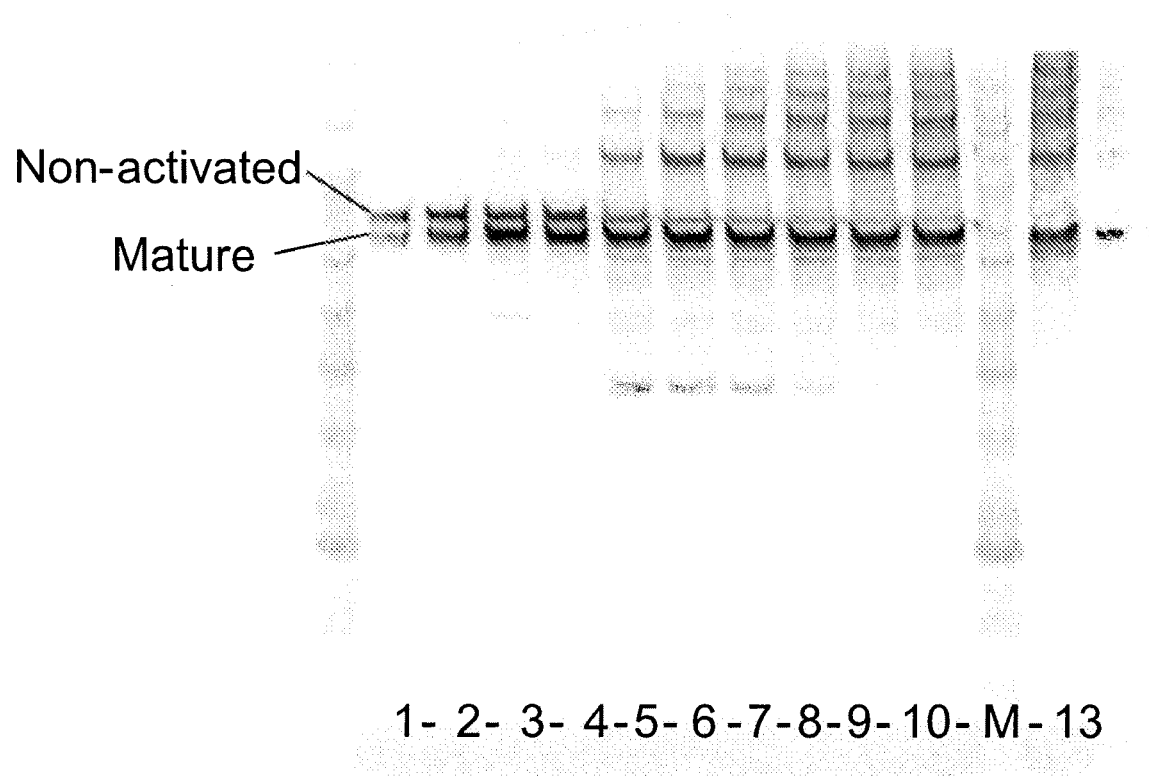
FIG. 7. Activation of recombinant ecarin in cell cultures over time, assayed by SDS-PAGE.

Samples from culture supernatants were also separated by SDS-PAGE and blotted to nitrocellulose membranes. Labelling of the membrane was performed with polyclonal rabbit serum directed towards the mature part of ecarin expressed as inclusion bodies in E. coli. "M" indicates the molecular weight marker and numbers refer to day of sample collection. As can be seen from FIG. 7 the recombinant ecarin remains stable for more than a week after the death of the cells. Activation of ecarin may also take place at lower temperatures, for instance as low as room temperature, but will then require longer times for activation. Ecarin will remain stable for severable months in room temperature in the presence of dead host cells. The activity will increase gradually until it levels out. A decrease in activity has not been observed except in the presence of bacterial infections or high temperatures. Efforts to use trypsin for activation of ecarin were made, but were not successful.

Example 3

Conversion of Prothrombin to Thrombin by Ecarin

The ecarin protease converts prothrombin to meizothrombin, an intermediate form of thrombin that has thrombin catalytic activity. Further processing into thrombin is achieved by auto-catalyses. To determine the estimated amount of ecarin culture needed for converting prothrombin into thrombin, we performed a series of test digests. Different amounts of ecarin-containing culture supernatants as obtained in Example 2, were mixed with 1 mg/ml prothrombin (as obtained in example 1) in PBS buffer (Cambrex). Incubation of the mixtures was done at 37° C. for 1-3 hours. Samples were then analysed by SDS-PAGE to identify the amount of recombinant ecarin needed for complete conversion of prothrombin into thrombin. By this procedure we found that the recombinant ecarin was very potent; one liter of ecarin culture supernatant at 7000 U/L is capable of complete conversion of 64 grams of prothrombin into thrombin in less than 3 hours at 37° C. Normally recombinantly produced prothrombin has to be purified in order to separate fully-carboxylated prothrombin from the incompletely carboxylated prothrombin. However this is not necessary for the present invention as the recombinant ecarin is able to efficiently activate both the fully carboxylated and the incompletely carboxylated prothrombins.

Example 4

Purification of Thrombin

Figure 8:
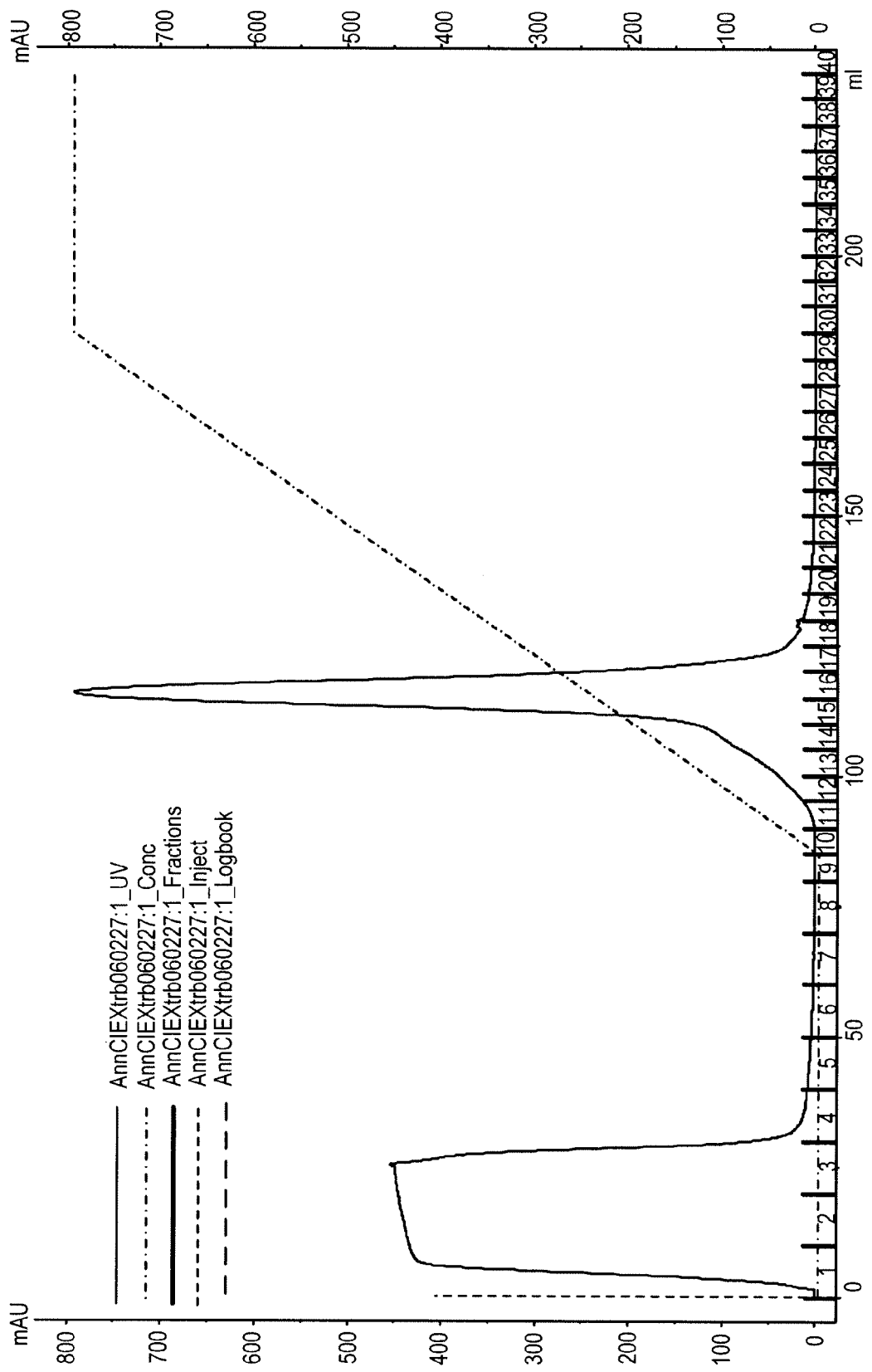
FIG. 8. Chromatogram from CIEX purification of rh-thrombin.
Figure 9:
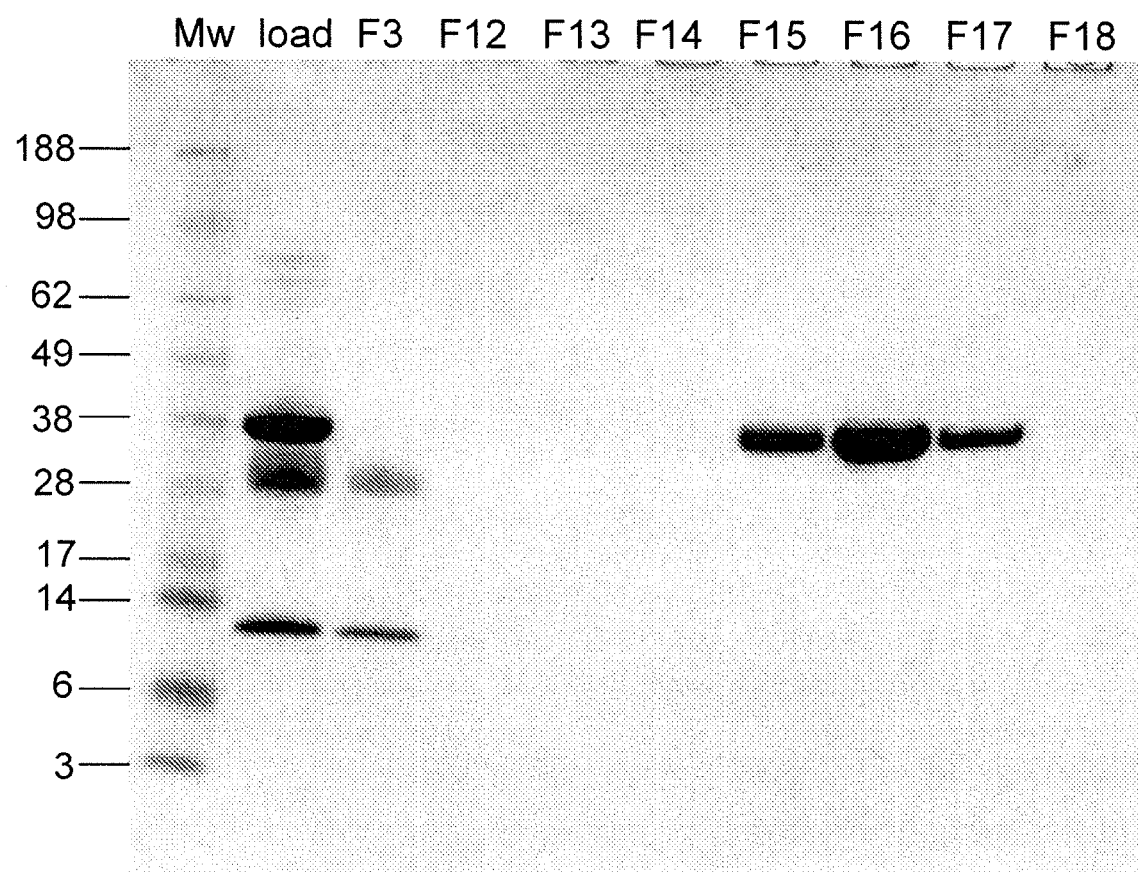
FIG. 9. Non-reduced SDS-PAGE analyses of fractions obtained by CIEX purification.

Thrombin obtained by the procedure described in example 3 was purified by cation-exchange chromatography (CIEX) using ÄKTA-FPLC (GE Healthcare) and an SP-Sepharose HP column (GE Healthcare) equilibrated with 25 mM sodium-phosphate buffer, pH 6.5. Ecarin-digested prothrombin prepared as in example 3 was adjusted to pH 6.2 and a conductivity of approximately 8 mS/cm. Thrombin was eluted with a 1M sodium chloride gradient in column equilibration buffer over 20 column volumes (FIG. 8). Selected fractions were analysed by SDS-PAGE (FIG. 9). Thrombin activity was confirmed by incubation with the chromogenic thrombin substrate S-2238 (Chromogenix, Mölndal).

Example 5

Analyses of rh-thrombin Obtained

To further analyse the obtained thrombin, kinetic parameters were determined using the chromogenic thrombin substrate S-2366 (Chromogenix). Activity was estimated by titration with hirudin. The rh-thrombin was for all parameters; Activity, $K_{kat}$ and $V_{max}$, similar to plasma-derived human α-thrombin from Haematologic Technologies Inc. (Vermont, USA).

Purified thrombin was also subjected to N-terminal sequencing: Reduced thrombin heavy and light polypeptide chains were separated by SDS-PAGE and blotted to Immobilon P membrane (Millipor). The excised bands were sequenced by the Edman degradation method. Heavy chain N-terminal first five amino acids were confirmed to be IVEGS, and the light chain five N-terminal amino acids were TFGS as expected.

The invention claimed is:

1. A method comprising:
   (a) providing mammalian cells comprising DNA encoding prepro-ecarin comprising SEQ ID NO:5;
   (b) expressing the prepro-ecarin in the cells by incubating the cells under conditions permitting the cells to express the prepro-ecarin from the DNA;
   (c) continuing to incubate the cells until substantially all of the cells have ceased to be viable, thereby producing a medium comprising dead cells; and
   (d) continuing to incubate the medium for an activation period sufficient to produce active ecarin from the prepro-ecarin in the medium.

2. The method of claim 1, wherein the activation period of (d) lasts at least seven days after substantially all cells have ceased to be viable.

3. The method of claim 1, further comprising fractionating the active ecarin-containing medium of (d) to separate a fraction containing active ecarin from a fraction containing dead cells.

4. The method of claim 1, wherein the cells are stably transfected with the DNA encoding prepro-ecarin.

5. The method of claim 1, wherein the DNA encoding prepro-ecarin comprises the nucleotide sequence of SEQ ID NO:2.

6. The method of claim 1, wherein the cells are CHO-S cells.

7. The method of claim 6, wherein the CHO-S cells are stably transfected with a DNA comprising the nucleic acid sequence of SEQ ID NO:2.

8. The method of claim 1, further comprising:
   providing recombinant human prothrombin; and
   contacting a sample of the active ecarin-containing medium with the recombinant human prothrombin, thereby producing recombinant human thrombin.

9. The method of claim 8, wherein the recombinant human prothrombin and the prepro-ecarin are expressed using cultured mammalian cells obtained from the same parental cell line.

10. The method of claim 9, wherein the parental cell line is CHO-S.

11. The method of claim 10, wherein the cells of (a) are CHO-S cells stably transfected with a DNA comprising the nucleic acid sequence of SEQ ID NO:2.

12. The method of claim 8, wherein the recombinant human prothrombin is a mixture of fully carboxylated prothrombin and incompletely carboxylated prothrombin.

13. The method of claim 8, wherein the recombinant prothrombin is fully carboxylated.

14. The method of claim 8, wherein the recombinant prothrombin is incompletely carboxylated.

15. The method of claim 8, further comprising purifying the recombinant human thrombin.

16. The method of claim 15, further comprising formulating the purified recombinant human thrombin in a pharmaceutical composition.

17. The method of claim 9, wherein the cultured mammalian cells expressing recombinant human prothrombin also comprise recombinant DNA encoding a gamma-glutamyl carboxylase and express recombinant gamma-glutamyl carboxylase.

18. The method of claim 17, wherein the level of expression of prothrombin by the cells expressing recombinant human prothrombin is at least ten times the level of expression of gamma-glutamyl carboxylase.

19. The method of claim 17, wherein the mammalian cells expressing recombinant human prothrombin express the recombinant prothrombin and recombinant gamma-glutamyl carboxylase while being cultured in a medium to which no vitamin K has been added.

20. The method of claim 17, wherein the recombinant prothrombin expressed in the cells expressing recombinant human prothrombin is incompletely carboxylated prothrombin or a mixture of fully and incompletely carboxylated prothrombin.

21. The method of claim 18, wherein the recombinant prothrombin expressed in the cells expressing recombinant human prothrombin is incompletely carboxylated prothrombin or a mixture of fully and incompletely carboxylated prothrombin.

22. The method of claim 19, wherein the recombinant prothrombin expressed in the cells expressing recombinant human prothrombin is incompletely carboxylated prothrombin or a mixture of fully and incompletely carboxylated prothrombin.

23. The method of claim 9, wherein the mammalian cells expressing recombinant human prothrombin express the recombinant prothrombin while being cultured in a medium to which no vitamin K has been added.

24. The method of claim 1, further comprising
producing, from the medium comprising dead cells, a culture supernatant comprising active ecarin; and
contacting prothrombin with the culture supernatant, thereby producing thrombin.

25. The method of claim 24, wherein the prothrombin is incompletely carboxylated prothrombin.

26. The method of claim 24, wherein the prothrombin is a mixture of fully carboxylated prothrombin and incompletely carboxylated prothrombin.

27. The method of claim 1, further comprising producing, from the medium of (d), a culture supernatant comprising active ecarin.

28. The method of claim 27, further comprising
providing recombinant prothrombin; and
contacting part or all of the culture supernatant with the recombinant prothrombin, thereby producing recombinant thrombin.

29. The method of claim 1, further comprising
providing recombinant prothrombin; and
contacting the active ecarin with the recombinant prothrombin, thereby producing recombinant thrombin,
wherein the active ecarin is not purified from the medium prior to being contacted with the recombinant prothrombin.

30. The method of claim 27, further comprising
providing recombinant prothrombin; and
contacting the active ecarin with the recombinant prothrombin, thereby producing recombinant thrombin,
wherein the active ecarin is not purified from the culture supernatant prior to being contacted with the recombinant prothrombin.

31. The method of claim 1, wherein the DNA encoding prepro-ecarin comprises a nucleotide sequence at least 85% identical to SEQ ID NO:2.

32. The method of claim 1, wherein the DNA encoding prepro-ecarin comprises a nucleotide sequence at least 90% identical to SEQ ID NO:2.

33. The method of claim 1, wherein the DNA encoding prepro-ecarin comprises a nucleotide sequence at least 95% identical to SEQ ID NO:2.

34. The method of claim 1, wherein the DNA encoding prepro-ecarin comprises a nucleotide sequence at least 97% identical to SEQ ID NO:2.

35. The method of claim 1, wherein the DNA encoding prepro-ecarin comprises a nucleotide sequence at least 98% identical to SEQ ID NO:2.

36. The method of claim 1, wherein the DNA encoding prepro-ecarin comprises a nucleotide sequence at least 99% identical to SEQ ID NO:2.

* * * * *